United States Patent [19]

Hoegerle et al.

[11] Patent Number: 5,037,449
[45] Date of Patent: Aug. 6, 1991

[54] REACTIVE DYES, THEIR PREPARATION AND USE

[75] Inventors: Karl Hoegerle; Urs Lehmann, both of Basle, Switzerland

[73] Assignee: Ciba-Geigy Corporation, Ardsley, N.Y.

[21] Appl. No.: 398,121

[22] Filed: Aug. 23, 1989

[30] Foreign Application Priority Data

Aug. 26, 1988 [CH] Switzerland ............ 3173/88

[51] Int. Cl.$^5$ .............. C09B 62/20; C09B 62/78; C07D 239/02; C07D 273/00

[52] U.S. Cl. ............................. 8/549; 8/543; 8/128.1; 8/116.1; 8/917; 544/298; 544/294; 544/65; 544/295

[58] Field of Search ............ 8/543, 549; 544/298, 544/294, 295, 65

[56] References Cited

U.S. PATENT DOCUMENTS

| | | | |
|---|---|---|---|
| 4,287,342 | 9/1981 | Hoegerle | 544/298 |
| 4,435,181 | 3/1984 | Hoguet et al. | 8/549 |
| 4,515,598 | 5/1985 | Meininger et el. | 8/549 |
| 4,581,036 | 4/1986 | Opitz et al. | 8/549 |
| 4,877,413 | 10/1989 | Sire et al. | 8/543 |

FOREIGN PATENT DOCUMENTS

| | | | |
|---|---|---|---|
| 0087703 | 9/1983 | European Pat. Off. | 8/549 |
| 0242324 | 10/1987 | European Pat. Off. | 8/549 |
| 2119234 | 4/1972 | France | 544/298 |

Primary Examiner—Paul Liberman
Assistant Examiner—J. Darland
Attorney, Agent, or Firm—George R. Dohmann; Edward McC. Roberts

[57] ABSTRACT

Reactive dyes of the formula

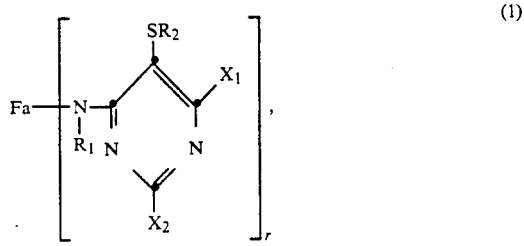

in which Fa is the radical of an organic dye of the monoazo or polyazo, metal complex azo, anthraquinone, phthalocyanine, formazan, azomethine, dioxazine, phenazine, stilbene, triphenylmethane, xanthene, thioxanthone, nitroaryl, naphthoquinone, pyrenequinone or perylene-tetracarbimide series, $X_1$ and $X_2$, independently of one another, are each halogen, $R_1$ is hydrogen or substituted or unsubstituted $C_1$–$C_4$alkyl, $R_2$ is substituted or unsubstituted $C_1$–$C_4$alkyl and r is the number 1 or 2, produce on hydroxyl- or nitrogen-containing textile materials dyeings which have good fastness properties.

19 Claims, No Drawings

REACTIVE DYES, THEIR PREPARATION AND USE

The present invention relates to novel reactive dyes, processes for their preparation and their use for the dyeing or printing of fibre materials.

The invention relates to reactive dyes of the formula

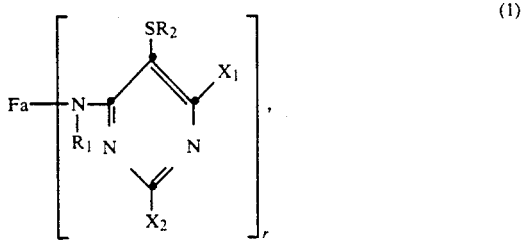

in which Fa is the radical of an organic dye of the monoazo or polyazo, metal complex azo, anthraquinone, phthalocyanine, formazan, azomethine, dioxazine, phenazine, stilbene, triphenylmethane, xanthene, thioxanthone, nitroaryl, naphthoquinone, pyrenequinone or perylene-tetracarbimide series, $X_1$ and $X_2$, independently of one another, are each halogen, $R_1$ is hydrogen or substituted or unsubstituted $C_1$–$C_4$alkyl, $R_2$ is substituted or unsubstituted $C_1$–$C_4$alkyl and r is the number 1 or 2.

The radical Fa in formula (1) can contain, bound to its basic structure, the substituents customary for organic dyes.

Examples of suitable substituents in the radical Fa are: unsubstituted or sulfo-substituted $C_1$–$C_4$alkyl, which in general comprises methyl, ethyl, n- or isopropyl or n-, sec- or tert-butyl; $C_1C_4$alkoxy, which in general is understood to mean methoxy, ethoxy, n- or isopropoxy or n-, sec- or tert-butoxy; $C_1$–$C_4$alkanoylamino, in particular acetylamino or propionylamino; benzoylamino; amino; N-mono- or N,N-di-$C_1$–$C_4$alkylamino, in which the alkyl can be further substituted, for example by —OH, —OCOCH$_3$, —OSO$_3$H, —CN or halogen, for example methylamino, ethylamino, n- or isopropylamino, n-, sec- or tert-butylamino, N,N-di-$\beta$-hydroxyethyl-amino, N,N-di-$\beta$-sulfatoethylamino, hydroxypropylamino, $\beta$-sulfatoethyl-amino, $\beta$-chloroethylamino, $\beta$-acetyloxyethylamino,; unsubstituted or sulfo- and/or $C_1$–$C_4$alkyl-substituted phenylamino; mono-· or di-sulfobenzylamino; $C_1$–$C_4$alkoxycarbonyl, for example methoxycarbonyl or ethoxycarbonyl; $C_1$–$C_4$alkylsulfonyl, for example methylsulfonyl or ethylsulfonyl; trifluoromethyl; nitro; cyano; halogen, which in general is understood to mean fluorine, chlorine and bromine; phenyl, carbamoyl; N-mono- or N,N-di-$C_1$–$C_4$alkylcarbamoyl; sulfamoyl; N-mono- or N,N-di$C_1$–$C_4$alkylsulfamoyl; N-($\beta$-hydroxyethyl)sulfamoyl; N,N-di-($\beta$-hydroxyethyl)sulfamoyl; N-phenylsulfamoyl; hydroxyl; carboxyl; sulfo; sulfomethyl; ureido.

Fa is preferably the radical of an organic dye of the monoazo or polyazo, metal complex azo, anthraquinone, phthalocyanine, formazan or dioxazine series, which can be substituted by one or more of the above-mentioned radicals.

The radical Fa particularly preferably contains one or more sulfo groups and can furthermore be further substituted by one or more of the above-mentioned radicals.

Examples of suitable $R_1$ as $C_1$–$C_4$alkyl are: methyl, ethyl, propyl, isopropyl, butyl, tert-butyl, isobutyl, sec-butyl and the corresponding radicals which are substituted, for example, by halogen, hydroxy, cyano, carboxy, sulfo, sulfato, $C_1$–$C_4$alkoxycarbonyl or $C_1$–$C_4$alkoxy, for example carboxymethyl, $\beta$-carboxyethyl, methoxycarbonylmethyl, ethoxycarbonyl-methyl, $\beta$-methoxyethyl, $\beta$-ethoxyethyl, $\beta$-chloroethyl, $\gamma$-bromopropyl, $\gamma$-chloropropyl, $\beta$-hydroxyethyl, $\beta$-hydroxybutyl, $\beta$-cyanoethyl, sulfomethyl, $\beta$-sulfoethyl, $\beta$-sulfatoethyl.

$R_1$ is preferably methyl or ethyl and in particular hydrogen.

Examples of suitable $R_2$ as $C_1$–$C_4$alkyl are methyl, ethyl, propyl, isopropyl, butyl, tert-butyl, isobutyl, sec-butyl, and the corresponding radicals, which are substituted, for example, by halogen, for example fluorine, chlorine or bromine, or phenyl.

$R_2$ is preferably unsubstituted or halogen-, in particular chlorine-, or phenyl-substituted methyl or ethyl. $R_2$ is particularly preferably methyl, monochloromethyl or benzyl.

$X_1$ and $X_2$, independently of one another, are each halogen, for example fluorine, chlorine or bromine, in particular fluorine or chlorine.

A preferred group of reactive dyes according to the invention comprises compounds of the formula (1) in which $X_1$ and $X_2$ are each fluorine or chlorine.

The reactive dyes of the formula (1) can contain one or two fibre-reactive groups. Where r in formula (1) is the number 2, the two reactive radicals can be identical or different; preferably, both radicals are identical.

Reactive dyes of the formula (1) in which r is the number 1 are particularly preferred.

The compounds of the formula (1) are fibre-reactive. Fibre-reactive compounds are understood to mean those which are capable of reacting with the hydroxy groups of cellulose, the amino, carboxyl, hydroxyl and thiol groups of wool and silk, or with the amino and possibly carboxyl groups of synthetic polyamides to form covalent chemical bonds.

A preferred group of reactive dyes according to the invention comprises compounds of the formula (1) mentioned in which Fa is the radical of an organic dye of the monoazo or polyazo, metal complex azo, anthraquinone, phthalocyanine, formazan or dioxazine series, which carries one or several sulfo groups and may be further substituted by one or more of the abovementioned radicals, $R_1$ is hydrogen or unsubstituted or, for example, halogen-, hydroxyl-, cyano-, carboxyl-, sulfo-, sulfato-, $C_1$–$C_4$alkoxycarbonyl or $C_1$–$C_4$alkoxy-substituted $C_1$–$C_4$alkyl, $X_1$ and $X_2$, independently of one another, are each fluorine or chlorine, $R_2$ is unsubstituted or halogen-, in particular chlorine-, or phenyl-substituted methyl or ethyl and r is the number 1.

A particularly preferred embodiment of the present invention relates to reactive dyes of the formula

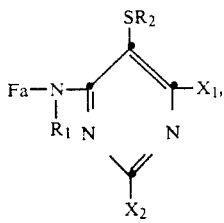 (2)

in which Fa has the abovementioned meanings and preferences, $R_1$ is hydrogen, methyl or ethyl, $X_1$ and $X_2$ are each chlorine or fluorine and $R_2$ is methyl, monochloromethyl or benzyl.

Preferred subgroups of the reactive dyes of the formula (1) are:

a) Monoazo or diazo dyes of the formula

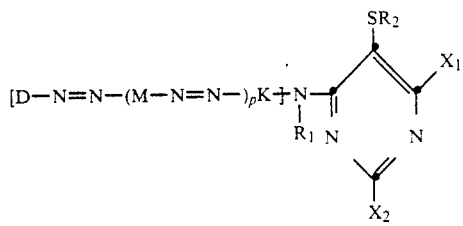 (3)

or of the formula

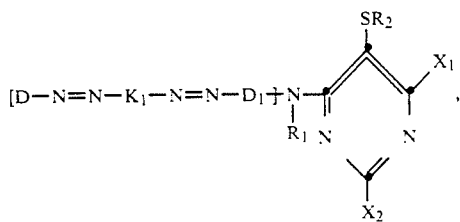 (4)

in which $R_1$, $R_2$, $X_1$ and $X_2$ each have the abovementioned meanings and preferences, D and $D_1$, independently of one another, are a diazo component of the benzene or naphthalene series or of the heterocyclic series, M is a middle component of the benzene or naphthalene series, K is a coupling component of the benzene or naphthalene series or of the heterocyclic series, $K_1$ is the radical of a coupling component of the aminonaphtholsulfonic acid series and p is the number 0 or 1.

Suitable subgroups of the reactive dyes of the formula (3) are: Compounds of the formula

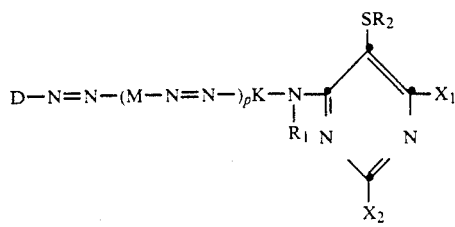 (5)

and compounds of the formula

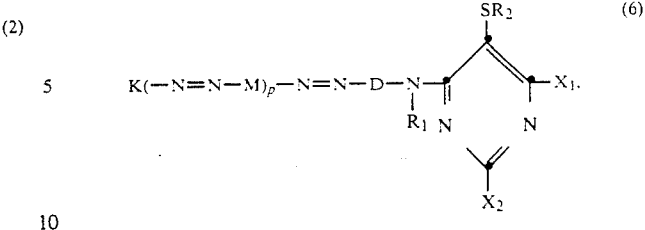 (6)

in which $R_1$, $R_2$, $X_1$, $X_2$, K, D, M and p are each as defined above.

The radicals D and $D_1$ can be derived, for example, from the following diazo components:

Aminobenzene, 1-amino-2-, -3- or -4-methylbenzene, 1-amino-2-, -3- or -4-methoxybenzene, 1-amino-2-, -3- or -4-chlorobenzene, 1-amino-2,5-dichlorobenzene, 1-amino-2,5-dimethylbenzene, 1-amino-3-methyl-6-methoxybenzene, 1-amino-2-methoxy-4-nitrobenzene, 1-aminobiphenyl, 1-aminobenzene-2-, -3- or -4-carboxylic acid, 2-aminodiphenyl ether, 1-amino-benzene-2-, -3- or -4-sulfonamide, 1-aminobenzene-2-, -3- or -4-sulfonic acid, 1-aminobenzene-2,4- and -2,5-disulfonic acid, 1-amino-4-methylbenzene-2-sulfonic acid, 1-amino-4-methoxybenzene-2-sulfonic acid, 1-amino-4-ethoxybenzene-2-sulfonic acid, 1-amino-3-methylbenzene-6-sulfonic acid, 1-amino-6-methylbenzene-3- or -4-sulfonic acid, 1-aminonaphthalene, 2-aminonaphthalene, 1-aminonapthalene-2-, -4-, -5-, -6-, -7- or -8-sulfonic acid, 2-aminonaphthalene-1-, -3-, -4-, -5-, -6-, -7-, or -8-sulfonic acid, 1-aminonapthalene-3,6- or -5,7-disulfonic acid, 2-aminonaphthalene-1,5-, -1,7-, -3,6-, -5,7-, -4,8- or -6,8-disulfonic acid, 1-aminonaphthalene-2,5,7-trisulfonic acid, 2-amino-naphthalene-1,5,7-, -3,6,8- or -4,6,8-trisulfonic acid, 2-amino-5-methylnaphthalene1-sulfonic acid, 4-aminoazobenzene-3,4'-disulfonic acid, 3-methoxy-4-amino-6-methylazobenzene-2',4'-disulfonic acid, 3-methoxy-4-amino-6-methylazobenzene-2',5'-disulfonic acid, 1-amino-4-β-sulfatoethylsulfonylbenzene, 1-amino-4-vinylsulfonylbenzene, 1-amino-3-vinylsulfonylbenzene, 1-amino-4-B-sulfatoethylsulfonylbenzene-2-sulfonic acid, 1-amino-4-[β-(β'-chloroethylsulfonyl)ethylaminocarbonyl]benzene-2-sulfonic acid, 1-amino-4-β-(vinylsulfonyl)ethylaminocarbonylbenzene-2-sulfonic acid, 1-amino-3-γ-(vinylsulfonyl)-butyrylaminobenzene-6-sulfonic acid, 1-amino-3-vinylsulfonyl-6-methoxybenzene, 1-amino-3-β-(vinyl-sulfonyl)ethylaminocarbonyl-6-methoxybenzene and 1-amino3-β-(vinyl-sulfonyl)ethylaminocarbonylbenzene; further diaminobenzenes or diamino-naphthalenes, such as 1,4-diaminobenzene-2-sulfonic acid, 1,4-diamino-benzene-2,5-disulfonic acid, 1,4-diaminobenzene-2,6-disulfonic acid, 1,3-diaminobenzene-4-sulfonic acid, 1,3-diaminobenzene-4,6-disulfonic acid, 1,4-diamino-2-chlorobenzene-5-sulfonic acid, 1,4-diamino-2-methylbenzene-5-sulfonic acid, 1,5-diamino-6-methyl-benzene-3-sulfonic acid, 1,3-diamino-6-methylbenzene-4-sulfonic acid, 1,4-diaminobenzene-2-carboxylic acid, 1,3-diaminobezene-4-carboxylic acid, 1-amino-3-aminomethylbenzene-6-sulfonic acid, 1-amino-3-aminomethyl-4-methoxy-benzene-2-sulfonic acid, 2,6-diaminonaphthalene-4,8-disulfonic acid, 2-amino-5-aminomethylnaphthalene-1-sulfonic acid and 2-amino-5-aminomethylnapthalene-1,7-disulfonic acid; instead of a diamine, it is also possible to use an aminoacetylamino compound, from which afterwards the acetyl group is again eliminated by hydrolysis, for example 1-acetylamino-3-aminobenzene-4-sulfonic acid or 1-acetylamino-4-aminobenzene-3-sulfonic acid.

Furthermore, D and $D_1$ are derived from, for example, thienyl, thiazolyl, isothiazolyl, 1,2,4-thiadiazolyl, 1,3,4-thiadiazolyl, benzothiazolyl, benzisothiazolyl, pyrazolyl, imidazolyl, 1,2,3-triazolyl, 1,2,4-triazolyl, thiophenyl, benzothiophenyl, tetrahydrobenzothiophenyl, pyridinyl, indazolyl, it being possible for each of the abovementioned radicals to be substituted, in particular by $C_1$–$C_8$alkyl, $C_1$–$C_8$alkoxy, $C_2$–$C_8$-alkanoylamino, $C_2$–$C_8$alkoxycarbonylamino, benzoylamino, amino, mono-or dialkylamino having 1 to 8 carbon atoms in the alkyl radical, phenylamino, $C_2$–$C_8$alkoxycarbonyl, nitro, cyano, trifluoromethyl, halogen, sulfamoyl, sulfamoyl which is monosubstituted or disubstituted on the nitrogen atom by $C_1$–$C_4$alkyl, $C_5$–$C_7$cycloalkyl or phenyl, carbamoyl, ureido, hydroxyl, $C_1$–$C_8$alkylsulfonyl, phenylsulfonyl, $C_1$–$C_4$alkyland/or sulfo- and/or halogen-substituted phenylsulfonyl or phenoxysulfonyl, carboxyl, sulfomethyl, sulfo, sulfato, thiosulfato and 2 adjacent substituents of the ring systems mentioned can each form further fused-on phenyl rings or cyclohexyl rings.

The radical M can be derived from, for example, the following middle components:
Aniline; m-toluidine;
2,5-dimethyl- or 2,5-dimethoxyaniline;
m-amino-anisole; m-acetylamino-,
m-propionylamino-, m-butyrylamino- or
m-benzoylaminoaniline;
m-aminophenylurea;
4-acetamino-2-aminotoluene or -anisole;
2-amino-4-methylanisole;
1-aminonaphthalene-6- or -7-sulfonic acid;
2-amino-4-acetylamino-benzenesulfonic acid;
2-amino-5-naphthol-7-sulfonic acid;
2-amino-8-naphthol-6-sulfonic acid;
2-(4-aminobenzoyl-amino)-5-naphthol-7-sulfonic acid;
3-sulfo-4-aminoacetanilide.

Of the large number of possible coupling components K and $K_1$, examples are as follows: phenol, 1-hydroxy-3- or -4-methylbenzene, 1-hydroxybenzene-4-sulfonic acid, 1-hydroxynaphthalene, 2-hydroxynaphthalene, 2-hydroxynaphthalene-6- or -7-sulfonic acid, 2-hydroxynaphthalene-3,6- or -6,8-disulfonic acid, 1-hydroxynaphthalene-4-sulfonic acid, 1-hydroxynapthalene-4,6-or -4,7-disulfonic acid 1-amino-3-methyl-benzene, 1-amino-2-methoxy5-methylbenzene, 1-amino-2,5-dimethylbenzene, phenyl urea, 3-aminophenylurea, 1-amino-3-acetylaminobenzene, 1-amino-3-hydroxyacetylaminobenzene, 1,3-diaminobenzene-4-sulfonic acid, 1-aminonaphthalene-6or -8-sulfonic acid, 1-amino-2-methoxynaphthalene-6-sulfonic acid, 2-aminonaphthalene-5,7-disulfonic acid, 1-amino-8-hydroxynaphthalene-4-sulfonic acid, 1-amino-8-hydroxy-naphthalene-6-sulfonic acid, 1-amino-8-hydroxynaphthalene-2,4-disulfonic acid, 2-hydroxy-3-aminonaphthalene-5,7-disulfonic acid, 1-amino-8-hydroxy-naphthalene-2,4,6-trisulfonic acid, 1-hydroxy-8-acetylaminonaphthalene-3-sulfonic acid, 1-benzoylamino-8-hydroxynaphthalene-3,6- or -4,6-disulfonic acid, 1,7-dihydroxynaphthalene-3-sulfonic acid, 2-benzoyl-amino-5-hydroxynaphthalene-7-sulfonic acid, 2-amino-5-hydroxy-naphthalene-7-sulfonic acid, 2-methyl- or 2-ethylamino-5-hydroxy-naphthalene-7-sulfonic acid, 2-(N-acetyl-N-methylamino)-5-hydroxy-naphthalene-7-sulfonic acid, 2-acetylamino-5-hydroxynaphthalene-7-sulfonic acid, 2-amino-5-hydroxynaphthalene-1,7-disulfonic acid, 2-amino-8-hydroxynaphthalene-6-sulfonic acid, 2-methyl- or -2-ethylamino-8-hydroxynaphthalene-6-sulfonic acid, 2-(N-acetyl-N-methylamino)-8-hydroxynaphthalene-6-sulfonic acid, 2-acetylamino-8-hydroxynaphthalene-6-sulfonic acid, 2-amino-8-hydroxynaphthalene-3,6-disulfonic acid, 2-acetylamino-8-hydroxynaphthalene3,6-disulfonic acid, 1-amino-5-hydroxynaphthalene-7-sulfonic acid, 1-amino-8-hydroxynapthalene-3,6- or -4,6-disulfonic acid, 1-acetylamino-8-hydroxynaphthalene-3,6or -4,6-disulfonic acid, 1-acetylamino-8-hydroxynaphthalene-3,6-or -4,6-disulfonic acid, 1-(4'-aminobenzoylamino)-8-hydroxynaphthalene-3,6-or -4,6-disulfonic acid, 1-(4'-nitrobenzoylamino)-8-hydroxynaphthalene-3,6- or -4,6-disulfonic acid, 1-(3'-aminobenzoylamino)-8-hydroxy-naphthalene-3,6- or -4,6-disulfonic acid, 1-(3'-nitrobenzoylamino)-8-hydroxynaphthalene-3,6- or -4,6-disulfonic acid, 2-(4'-amino-3'-sulfophenylamino)-5-hydroxynaphthalene-7-sulfonic acid, 3-methyl-5-pyrazolone, 1-phenyl-3-methyl5-pyrazolone, 1-phenyl-3-methyl5-pyrazolone 1-(4'-sulfophenyl)-3-methyl-5-pyrazolone, 1-(4'-sulfophenyl)-5-pyrazolone-3-carboxylic acid, 1-(3'-aminophenyl)-3-methyl5-pyrazolone, 1-(2',5'-disulfophenyl)-3-methyl-5-pyrazolone, 1-(2'-methyl-4'sulfophenyl)-5-pyrazolone-3-carboxylic acid, 1-(4',8'-disulfonaphthyl-[2'])-3-methyl-5-pyrazolone, 1-(5',7'-disulfonaphthyl-[2'])-3-methyl-5-pyrazolone, 1-(2',5'-dichloro-4'-sulfophenyl)-3-methyl-5-pyrazolone, 3-aminocarbonyl-4-4-methyl-6-hydroxy-2-pryidone, 1-ethyl-3-cyano- or -3-chloro-4-methyl-6-hydroxy-2-pyridone, 1-ethyl-3-sulfomethyl-4-methyl-6-hydroxy-2-pyridone, 1-ethyl-3-sulfomethyl-4-methyl-6-hydroxy-2-pyridone, 2,4,6-triamino-3-cyanopyridine, 2-(3'-sulfophenylamino)-4,6-diamino-3-cyano-pyridine, 2-(2'-hydroxyethylamino)-3-cyano-4-methyl-6-aminopyridine, 2,6-bis-(2'-hydroxyethyl1-ethyl-3-carbamoyl-4-methyl-6-hydroxy2-pyridone, 1-ethyl-3-sulfomethyl-4-methyl-5-carbamoyl-6-hydroxy-2pyridone, 1-ethyl-3-sulfomethyl-4-methyl-6-hydroxy-2-pyridone, N-acetoacetylaminobenzene, 1-(N-acetoacetylamino)-2-methoxybenzene-5-sulfonic acid, 4-hydroxy-2-quinolone, 1-amino-8-hydroxy-2-(phenylazo)-naphthalene 3,6-disulfonic acid, 1-amino-8-hydroxy-2-(2',5'-disulfophenylazo)-naphthalene-3,6-disulfonic acid, 1-B-aminoethyl-3-cyano-4-methyl-6-hydroxy-2-pyridone, 1-γ-aminopropyl-3-sulfomethyl-4-methyl-6-hydroxy-2-pyridone, 1,3-diaminobenzene, 1-amino-3-N,N-di-β-hydroxyethylaminobenzene, 1-amino-3-N,N-di-β-sulfatoethyl-aminobenzene, 1-amino-3-N,N-di-β-hy droxyethylamino-4-methoxybenzene, 1-amino-3-N,N-di-B-sulfatoethylamino-4-methoxybenzene, 1-amino-3-sulfo-benzylamino-benzene, 1-amino-3-sulfo-benzylamino-4-chlorobenzene, 1-amino-3-N,N-disulfobenzylaminobenzene, N,N-di-(B-sulfatoethyl)-aniline, 3-acetylamino-N,N-di-(β-sulfatoethyl)-aniline, 3-methyl-N,N-di-(β-sulfatoethyl)aniline, N-ethyl-N-(β-hydroxyethyl)-aniline, N-ethyl-N-(B-acetoxyethyl)-aniline, 3-acetylamino-N,N-di(β-hydroxyethyl)-aniline, 3-methyl-N,N-di-(β-acetoxyethyl)-aniline, 2-methoxy-5-acetylamino-N-(β-acetoxyethyl)-N-benzylaniline, 2-chloro-5-acetylamino-N-(y-phenoxy-β-hydroxy-n-propyl)-aniline, 3-ureidoaniline, N-ethyl-N-(3'-sulfobenpropyl)-aniline, 3-methyl-N-ethyl-N-(β-sulfatoethyl)-aniline, 3-methyl-N,N-di-(β-hydroxyethyl)-aniline, 3-methyl-6-methoxy-N,N-di-(B-hydroxyethyl)aniline.

In the case where the reactive dyes have the formula (3) or (4) and accordingly $Fa-[-NR_1-]_r$ in formula (1) in which $R_1$ and r are as defined in formula (1) is the radical of a monoazo or diazo compound, this radical can be derived, for example, from the following organic monoazo or diazo dyes:
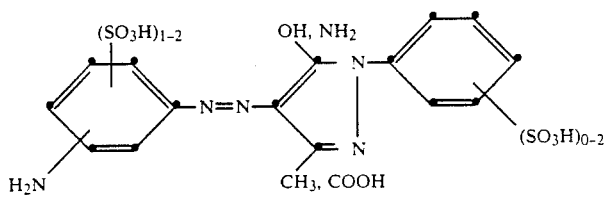 (7)
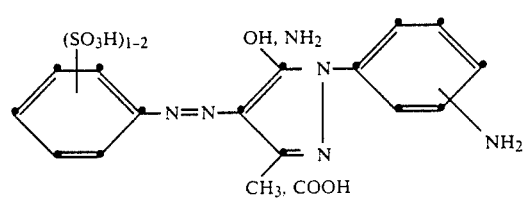 (8)
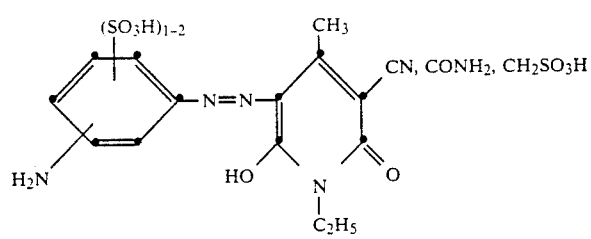 (9)
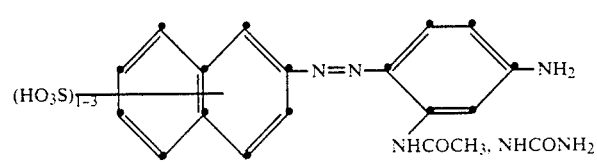 (10)
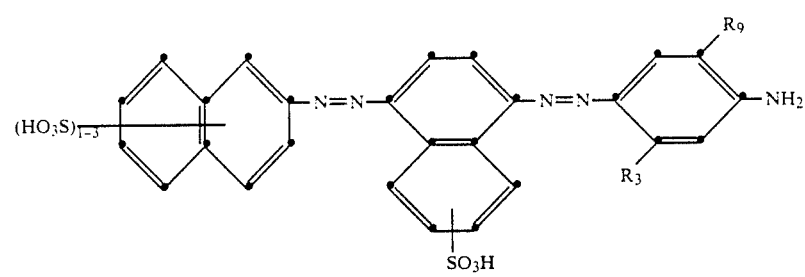 (11)
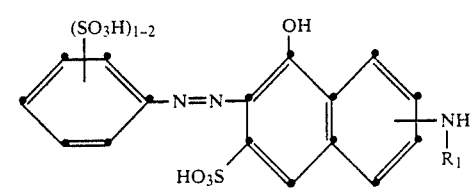 (12)
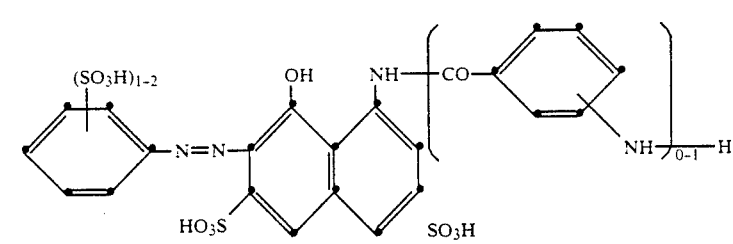 (13)

-continued
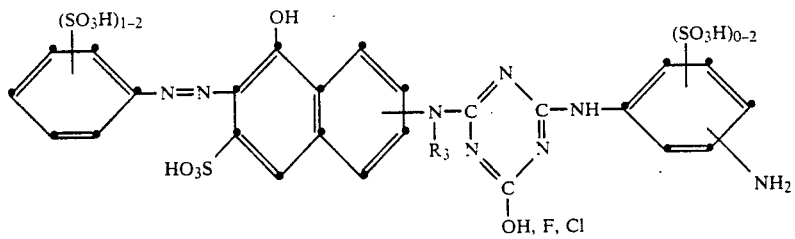
(14)
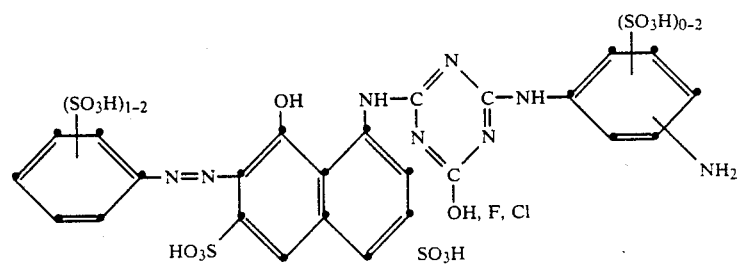
(15)
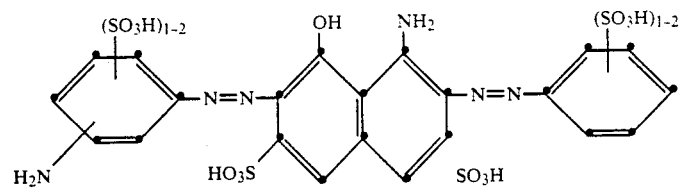
(16)
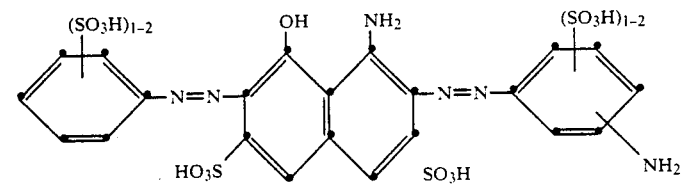
(17)
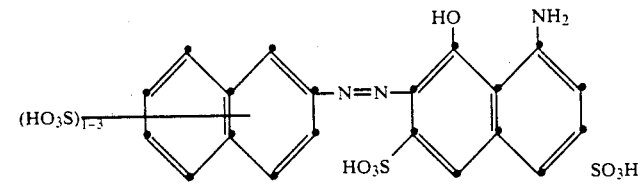
(18)
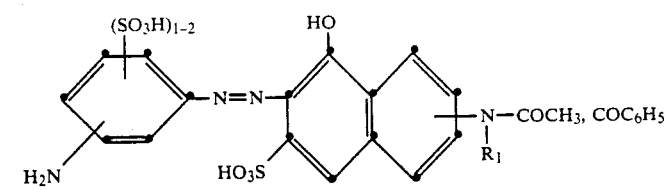
(19)
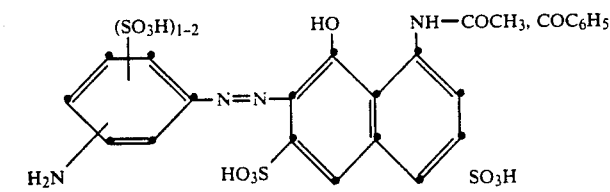
(20)
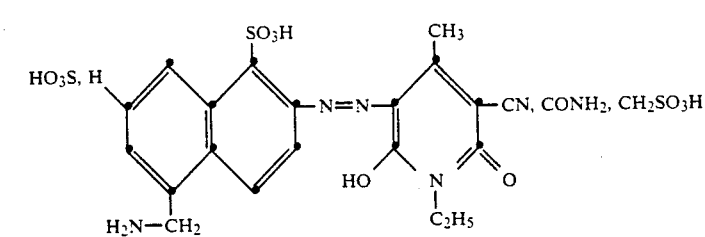
(21)

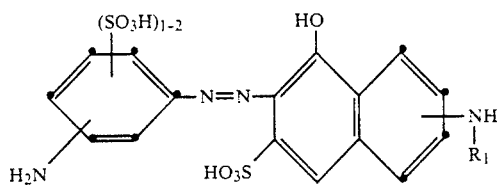
(22)
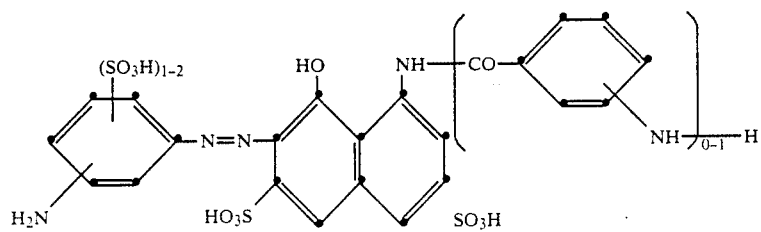
(23)
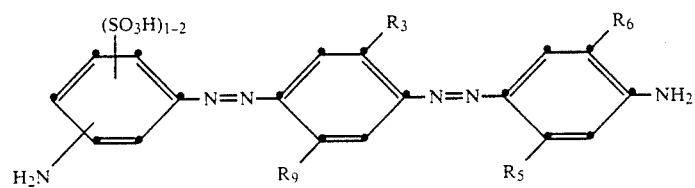
(24)
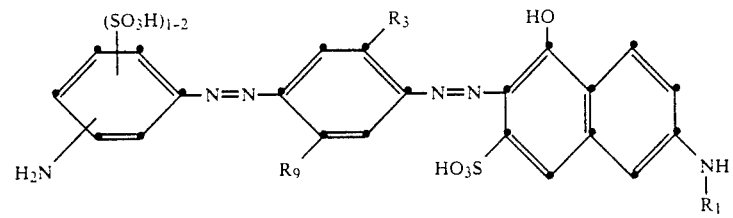
(25)
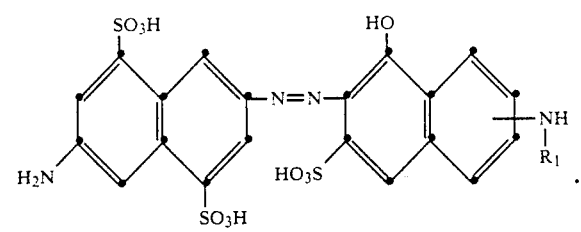
(26)
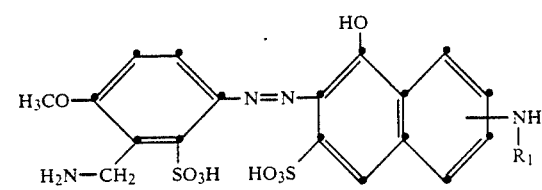
(27)
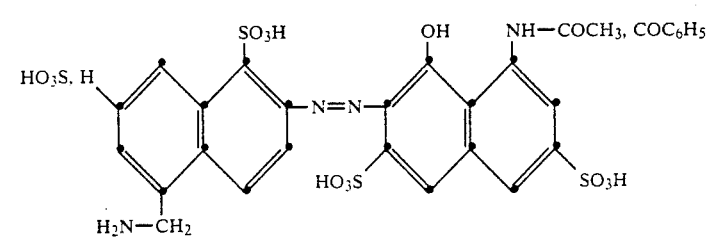
(28)

-continued

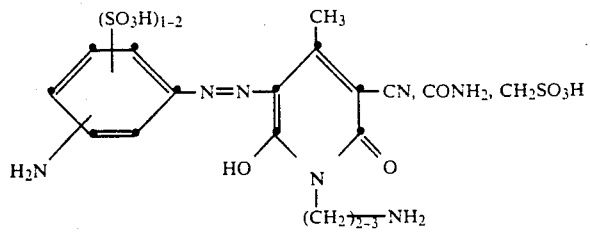 (29)

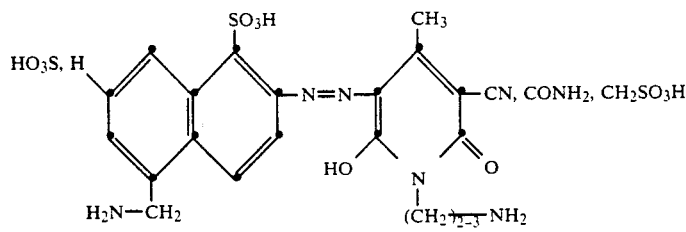 (30)

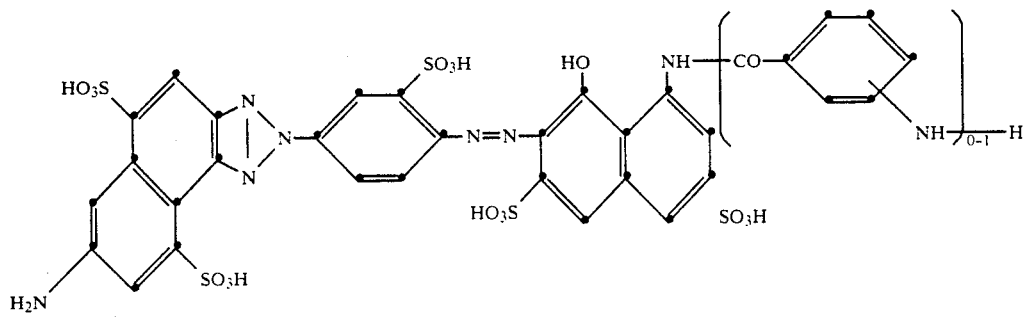 (31)

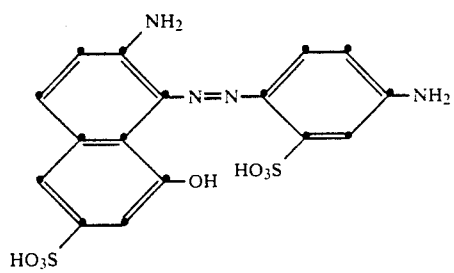 (32)

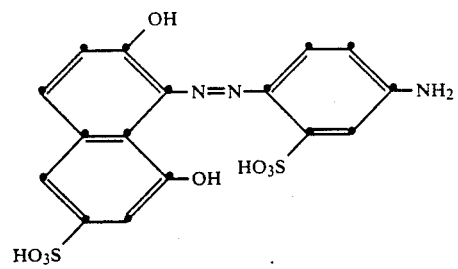 (33)

In the formulae (7) to (33), $R_3$, $R_5$, $R_6$ and $R_9$, independently of one another, are, for example, hydrogen, $C_1$-$C_4$alkyl, $C_1$-$C_4$alkoxy, $C_1$-$C_4$-alkanoylamino, ureido or halogen and $R_1$ is as defined in formula (1).

b) Metal complexes of monoazo or disazo dyes of the abovementioned formulae (3) or (4) which contain groups capable of metal complex formation, for example hydroxyl, carboxyl, amino or sulfo.

In the case where Fa—[—$NR_1$—]$_r$ in formula (1) in which $R_1$ and r are as defined in formula (1) is the radical of a metal complex azo dye, this radical can be derived, for example, from a metal complex of the dyes mentioned below:

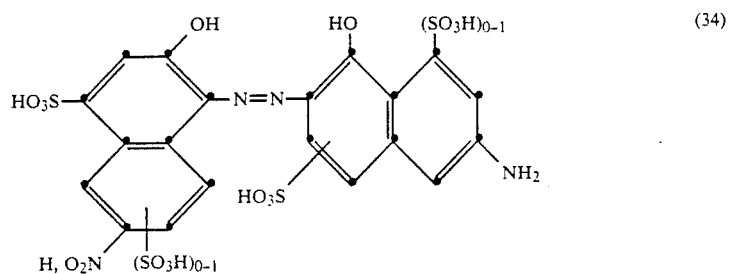
(34)
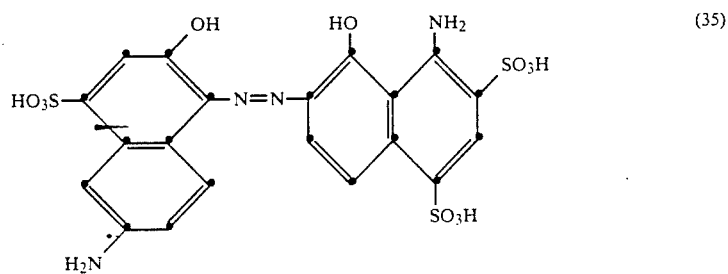
(35)
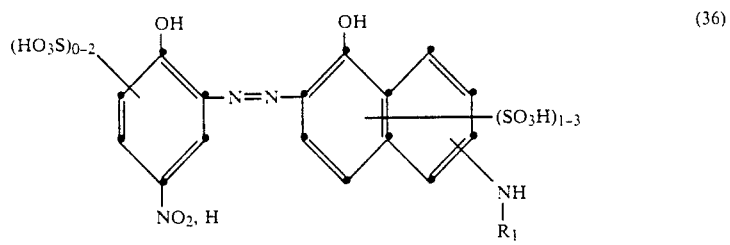
(36)
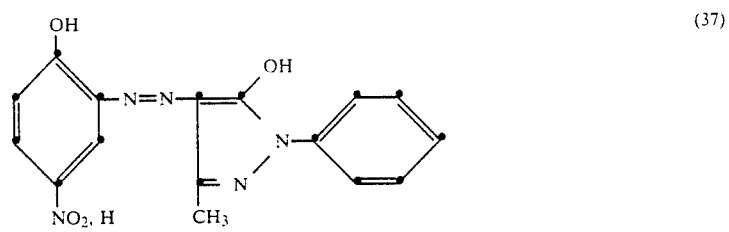
(37)
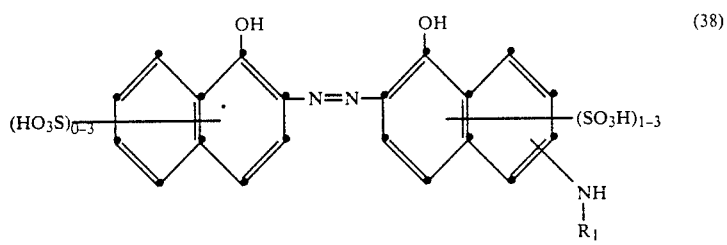
(38)
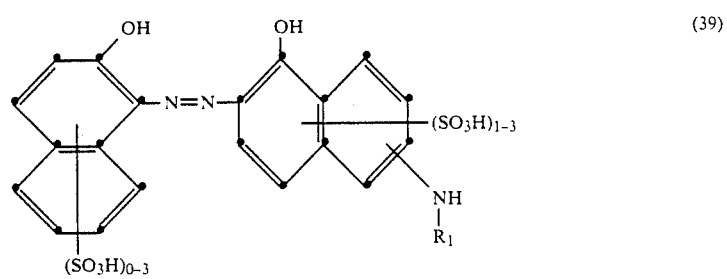
(39)

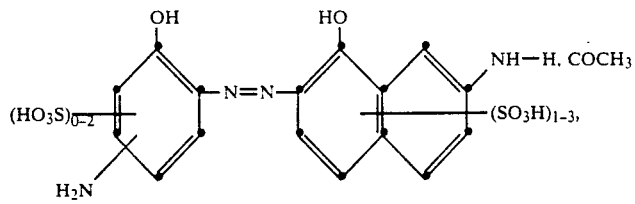

in which $R_1$ is as defined in formula (1).

The preferred metal atoms are Cu and Cr (1:1 complexes) or Cr and Co (1:2 complexes). Cr and Co complexes can contain the azo compounds of the formulae (34) to (40) once or twice, i.e. they can have a symmetrical or, in combination with any other desired ligans, an unsymmetrical structure.

Examples of suitable copper complex dyes on which the radical Fa—[—$NR_1$—]$_r$ in formula (1) in which $R_1$ and r are as defined in formula (1) can be based are:

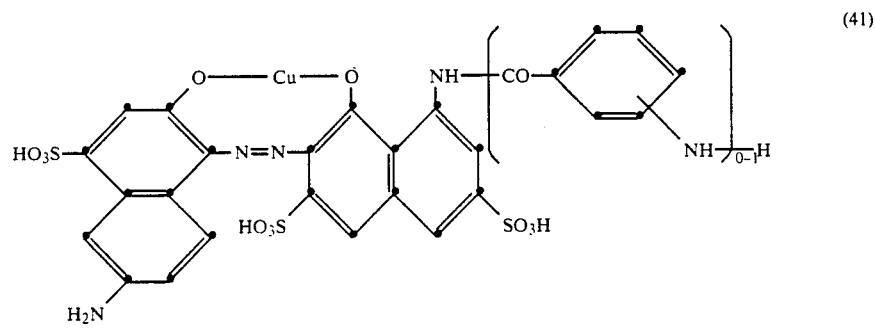

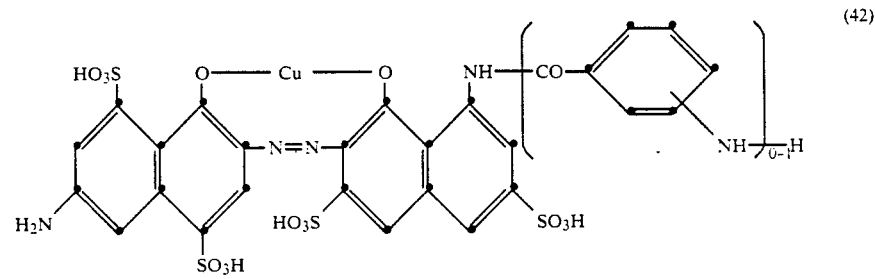

c) Antraquinone dyes of the formula

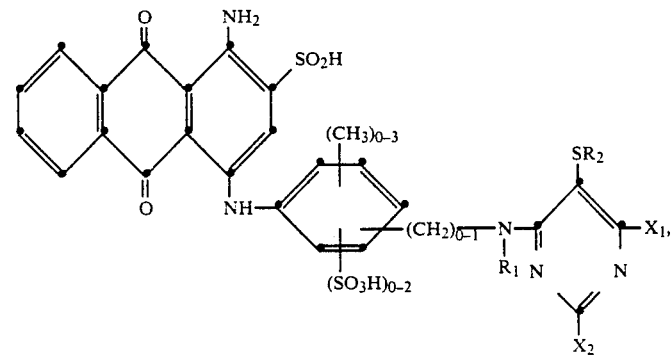

in which $R_1$, $R_2$, $X_1$ and $X_2$ are as defined in formula (1).

d) Formazan dyes of the formula

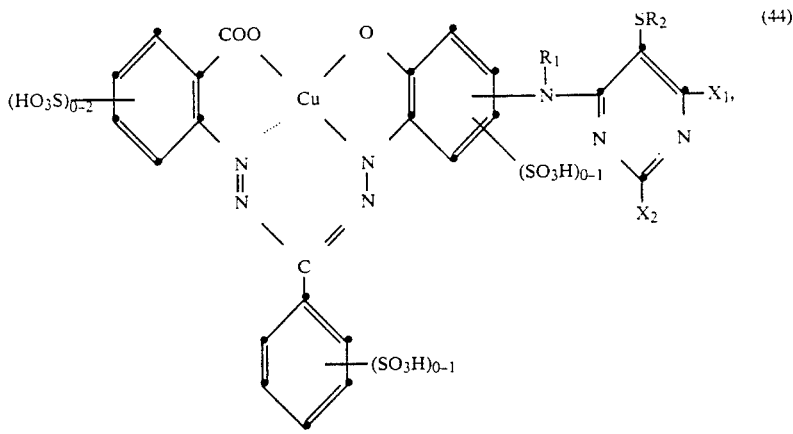

in which $R_1$, $R_2$, $X_1$ and $X_2$ are as defined in formula (1).

e) Phthalocyanine dyes of the formula

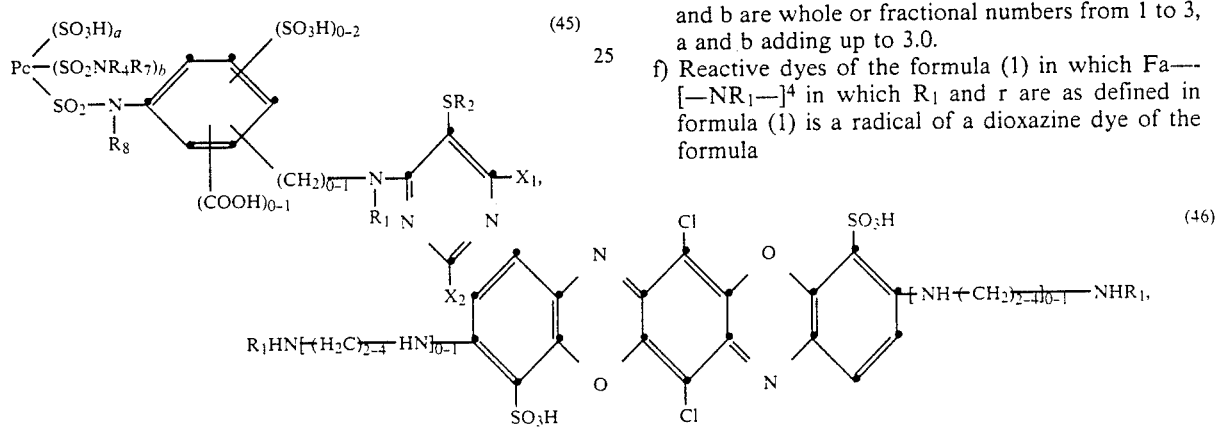

in which $R_1$, $R_2$, $X_1$ and $X_2$ are as defined in formula (1), Pc is the radical of a Cu or Ni phthalocyanine, $R_4$, $R_7$ and $R_8$, independently of one another, are $C_1$-$C_4$alkyl and in particular hydrogen, and a and b are whole or fractional numbers from 1 to 3, a and b adding up to 3.0.

f) Reactive dyes of the formula (1) in which Fa—$[-NR_1-]^4$ in which $R_1$ and r are as defined in formula (1) is a radical of a dioxazine dye of the formula in which $R_1$ is as defined in formula (1).

The following are very particularly preferred reactive dyes of the present invention:

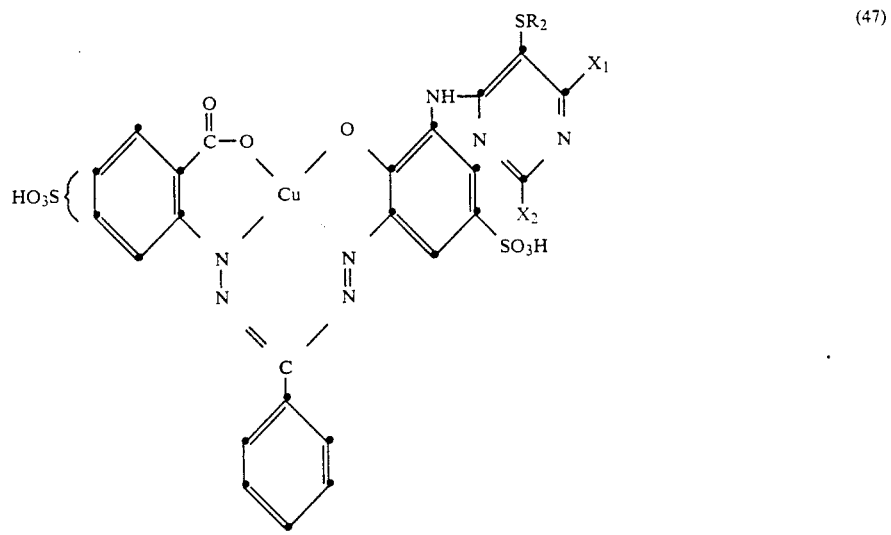

(48)
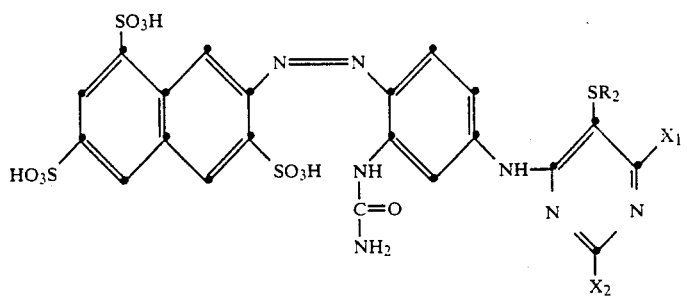
(49)
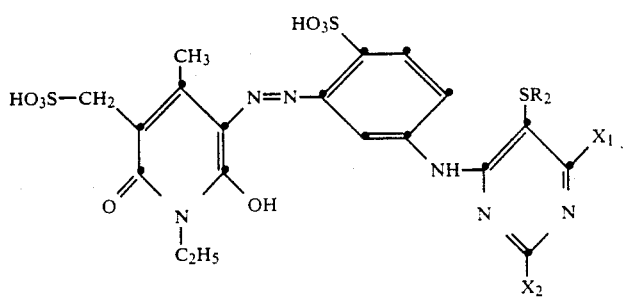
(50)
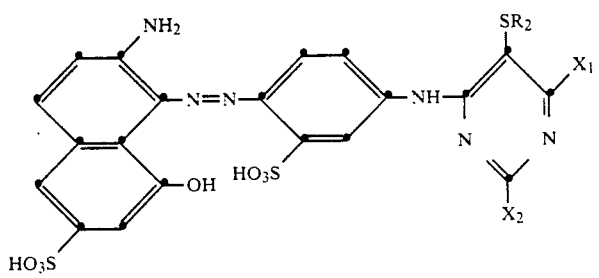
(51)
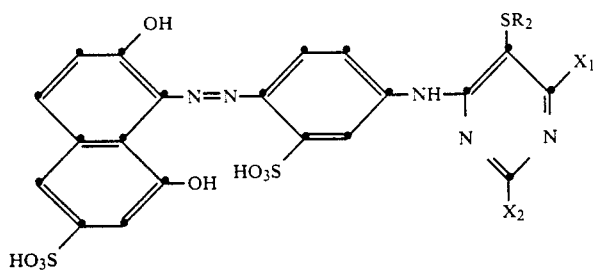
(52)
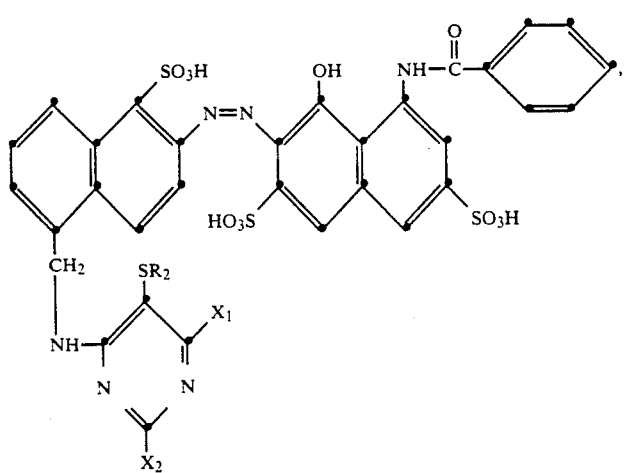

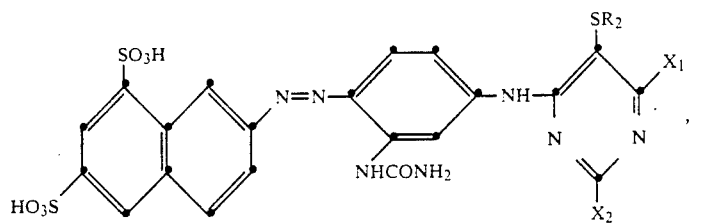
(53)
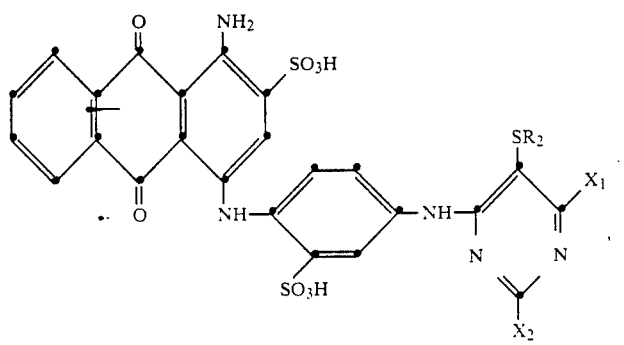
(54)
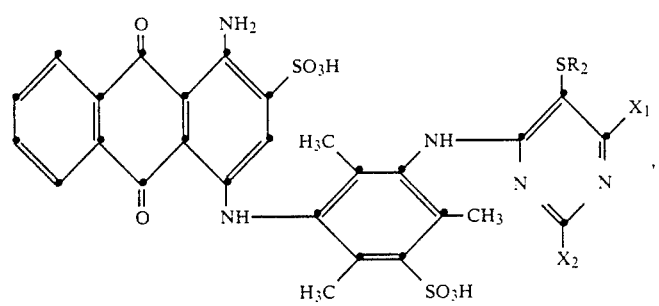
(55)
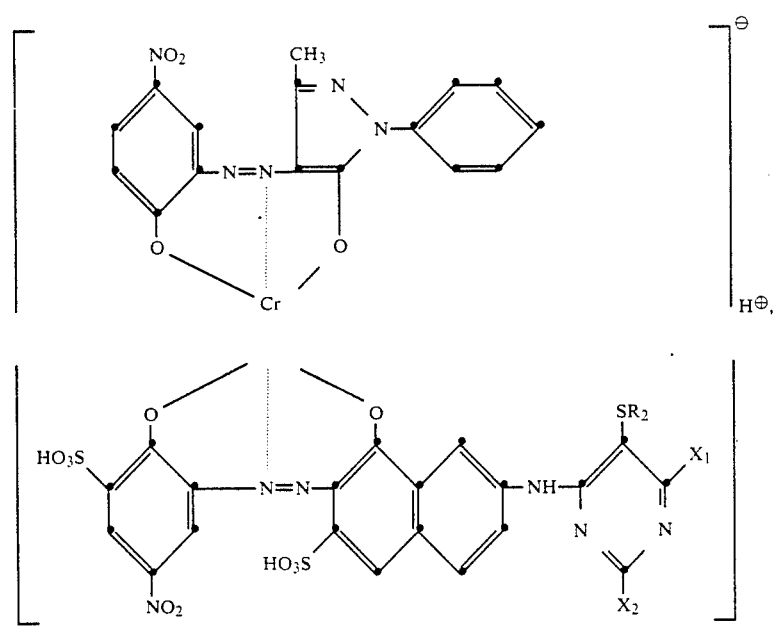
(56)

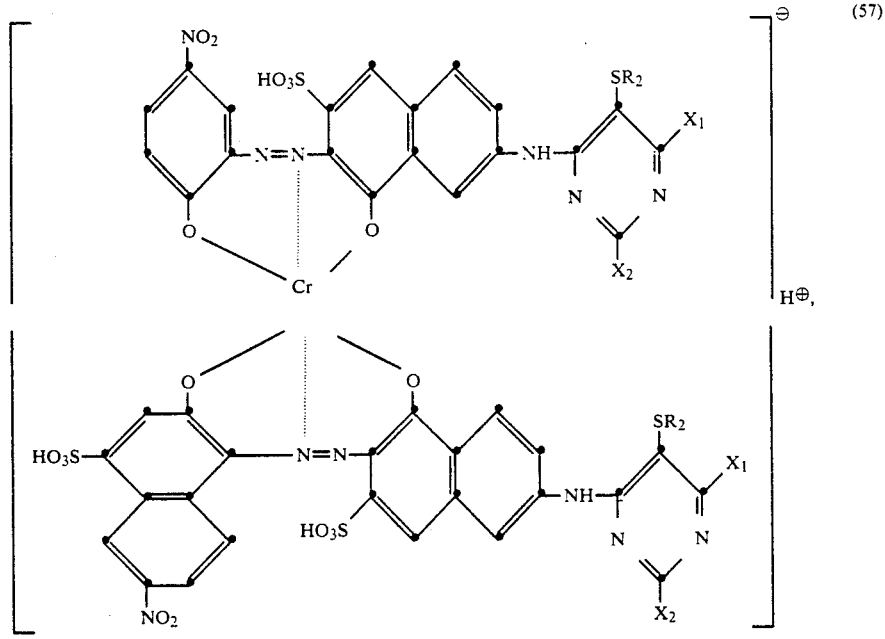

in which $R_2$, $X_1$ and $X_2$ are as defined in formula (1).

Of very particular value are reactive dyes of the formula (47) to (57) in which $X_1$ and $X_2$ are each fluorine or chlorine and $R_2$ is unsubstituted or halogen-, in particular chlorine-, or phenyl-substituted methyl.

The invention further relates to a process for the preparation of the reactive dyes according to the invention, which comprises condensing, for example, organic dyes of the formula

(58)

with at least one equivalent of a pyrimidine derivative of the formula

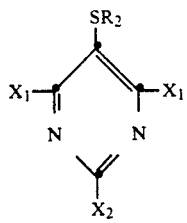
(59)

to a reactive dye of the formula (1) in which Fa, $R_1$, $R_2$, $X_1$, $X_2$ and r are as defined in formula (1).

The condensation of the dye of the formula (58) with a pyrimidine derivative of the formula (59) is preferably carried out in aqueous solution, emulsion or suspension, at low temperature, for example 0 to 40° C., and at a weakly acidic, neutral to weakly alkaline pH. Advantageously, the hydrohalide which is liberated in the condensation reaction is continuously neutralized by addition of aqueous alkali metal hydroxides, alkali metal carbonates, alkali metal bicarbonates or alkali metal acetates.

The most important embodiments are described in the Examples.

The compounds of the formula (58) are known per se and can be prepared in analogy to known compounds.

Some of the compounds of the formula (59) are known and can be prepared in analogy to known compounds.

Examples of suitable pyrimidine compounds of the formula (59) are:
2,4,6-trifluoro-5-methylthiopyrimidine,
2,4,6-trichloro-5-methylthiopyrimidine,
2,4,6-tribromo-5-methylthiopyrimidine,
2,4,6-trifluoro-5-ethylthiopyrimidine,
2,4,6-trichloro-5-ethylthiopyrimidine,
2,4,6-tribromo-5-ethylthiopyrimidine,
2,4,6-trifluoro-5-chloromethylthiopyrimidine,
2,4,6-trichloro-5-chloromethylthiopyrimidine,
2,4,6-tribromo-5-chloromethylthiopyrimidine,
2,4,6-trifluoro-5-β-chloroethylthiopyrimidine,
2,4,6-trichloro-5-β-chloroethylthiopyrimidine,
2,4,6-tribromo-5-β-chloroethylthiopyrimidine,
2,4,6-trifluoro-5-benzylthiopyrimidine,
2,4,6-trichloro-5-benzylthiopyrimidine,
2,4,6-tribromo-5-benzylthiopyrimidine,
2,4,6-trifluoro-5-phenethylthiopyrimidine,
2,4,6-trichloro-5-phenethylthiopyrimidine,
2,4,6-tribromo-5-phenethylthiopyrimidine,
2,4,6-trifluoro-5-dichloromethylthiopyrimidine,
2,4,6-trichloro-5-dichloromethylthiopyrimidine, The invention further relates to the compounds of the formula

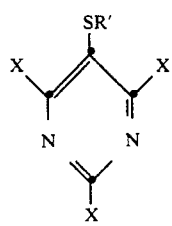
(60)

in which X is fluorine or chlorine and R' is chlorine- or phenyl-substituted $C_1$–$C_4$alkyl.

Compounds of the formula (60) in which X is fluorine or chlorine and R' is chlorine- or phenyl-substituted methyl or ethyl are preferred.

Compounds of the formula (60) in which X is fluorine or chlorine and R' is monochloromethyl or benzyl are very particularly preferred.

The invention also relates to a process for the preparation of the compounds of the formula (60) in which X and R' are as defined in formula (60), which comprises reacting barbituric acid with compounds of the formula

   (61)

in which R" is unsubstituted or chlorine- or phenyl-substituted $C_1$–$C_4$-alkyl in the presence of acetic anhydride to give compounds of the formula

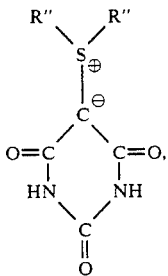   (62)

in which R" is as defined above, reacting the compounds of the formula (62) with halogen compounds of phosphorus in the presence of a catalyst at a temperature of 80° to 180° C., and in the case where R" is unsubstituted $C_1$–$C_4$alkyl chlorinating the radical R" and, in order to prepare compounds of the formula (60) in which X is fluorine and R' is as defined in formula (60) exchanging the halogen bound to the pyrimidine ring for fluorine by fluorination with a fluorinating agent.

One embodiment of the process according to the invention for the preparation of the compounds of the formula (60) in which X is fluorine or chlorine and R' is chlorine-substituted $C_1$–$C_4$alkyl consists in chlorinating unsubstituted $C_1$–$C_4$alkyl of a 2,4,6-trihalogeno-5-$C_1$–$C_4$alkylthiopyrimidine and, if desired, exchanging the halogen bound to the pyrimidine ring for fluorine by fluorination with a fluorinating agent.

Compounds of the formula (60) in which X is chlorine and R' is phenylsubstituted $C_1$–$C_4$alkyl can be obtained, for example, by condensation of barbituric acid with a compound of the formula (61) in which R" is phenyl-substituted $C_1$–$C_4$alkyl in the presence of acetic anhydride, followed by reaction with a chlorine compound of phosphorus.

Compounds of the formula (60) in which X is chlorine and R' is chlorinesubstituted $C_1$–$C_4$alkyl can be obtained, for example, by the process described above, starting from a compound of the formula (61) in which R" is unsubstituted $C_1$–$C_4$alkyl and subsequent chlorination of the unsubstituted $C_1$–$C_4$alkyl R", it also being possible to carry out the chlorination directly by starting from a 2,4,6-trichloro-5-$C_1$–$C_4$alkyl-thiopyrimidine, in which the $C_1$–$C_4$alkyl is unsubstituted.

Compounds of the formula (60) in which X is fluorine and R' is chlorine- or phenyl-substituted $C_1C_4$alkyl can be obtained, for example, starting from the trichloropyrimidine compounds prepared by the process described above by exchange of the chlorine bound to the pyrimidine ring for fluorine with a fluorinating agent.

A preferred embodiment of the process according to the invention for the preparation of compounds of the formula (60) comprises starting from compounds of the formula (61) in which R" is unsubstituted or phenylsubstituted methyl or ethyl, or, if desired, from 2,4,6-trichloro-5-methylthiopyrimidine or 2,4,6-trichloro-5-ethylthiopyrimidine.

A particularly preferred embodiment of the process according to the invention for the preparation of compounds of the formula (60) comprises starting from compounds of the formula (61) in which R" is unsubstituted or phenyl-substituted methyl, or, if desired, from 2,4,6-trichloro-5methylthiopyrimidine.

Examples of compounds of the formula (61) are dimethyl, diethyl, dipropyl, diisopropyl, dibutyl, di-tert-butyl, di-sec-butyl, diisobutyl, dibenzyl or diphenethyl sulfoxide.

The reaction of barbituric acid with compounds of the formula (61) in the presence of acetic anhydride is preferably carried out in organic solvents, for example acetonitrile, at temperatures of, for example, 60° to 120° C.

Examples of suitable halogen compounds of phosphorus, with which compounds of the formula (62) can be reacted, are phosphorus pentachloride, phosphorus trichloride or in particular phosphorus oxychloride. The reaction is preferably carried out at temperatures between 100° and 130° C. Examples of suitable catalysts are pyridine, triethylamine, tripropylamine, diethylaniline or in particular dimethylaniline.

The chlorination of the radical R", which is as defined above, is preferably carried out by means of chlorinating agents, for example chlorine gas, in organic solvents, for example carbon tetrachloride, at low temperatures, for example −40° to 5° C.

The fluorination is carried out by means of fluorinating agents, for example hydrogen fluoride, sodium fluoride, potassium fluoride or preferably a potassium fluoride/calcium fluoride mixture, the ratio of which is in particular 1:1, in organic solvents, for example sulfolane or preferably acetonitrile, at temperatures of, for example, 50° to 100° C.

The reactive dyes of the formula (1) according to the invention are suitable for the dyeing and printing of a large variety of materials, such as silk, leather, wool, polyamide fibres and cellulose-containing fibre materials of any kind. These fibre materials are, for example natural cellulose fibres, such as cotton, linen and hemp, and regenerated cellulose. The reactive dyes according to the invention are also suitable for the dyeing or printing of hydroxyl-containing fibres which are contained in mixed fabrics, for example mixtures of cotton with polyester fibres or polyamide fibres.

The reactive dyes of the formula (1) can be applied to the fibre material and fixed on the fibre in various ways, in particular in the form of aqueous dye solutions and printing pastes. They are suitable not only for the exhaust process but also for the dyeing by the padding dyeing process, in which the material is impregnated with aqueous dye solutions which may contain salt, and the dyes are fixed after an alkaline treatment or in the presence of alkali, if appropriate with the application of heat. They are particularly suitable for the so-called cold pad-batch process, in which the dye is applied together with alkali to the padder and then fixed at room temperature by leaving it for several hours. After fixing, the dyeings or prints are thoroughly rinsed with cold and hot water, if appropriate with the addition of an agent which acts as a dispersant and promotes the diffusion of the unfixed components.

The reactive dyes according to the invention are distinguished by high reactivity, and good fixation and build-up properties. They can therefore be used at low dyeing temperatures by the exhaust dyeing process and require only short steaming times in the pad-steam process. The degrees of fixation are high, and the unfixed components can easily be washed off.

The reactive dyes according to the invention are suitable for the dyeing and printing of hydroxyl- or nitrogen-containing textile materials, in particular for the dyeing and printing of cotton and wool, and produce dyeings which have good fastness properties.

The reactive dyes according to the invention are particularly suitable for the dyeing of wool. The dyeings have excellent wet fastness properties, in particular potting fastness properties.

The examples below serve to illustrate the invention. The temperatures are given in degrees centigrade, and the parts and percentages are by weight, unless stated otherwise. Parts by weight relate to parts by volume as to kilogram relates to the litre.

Example 1 b 9.18 parts of 2,4,6-trichloro-5-methylthiopyrimidine are dissolved in 60 parts of dry carbon tetrachloride, and 7.2 parts of chlorine gas are passed into this solution at $-20°$ over a period of 2 hours. The solution is then heated to $45°$, maintained at this temperature for 2 hours, then flushed with inert gas and distilled. This gives 10.1 parts of the compound of the formula

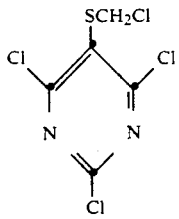

(101)

Example 2:

57 parts of dried acetonitrile are initially introduced. 46 parts of a potassium fluoride/calcium fluoride 1:1 mixture which has been dried at $150°$ in a high vacuum and 5.02 parts of the compound prepared according to Example 1 are then added.

The suspension is heated to reflux for 28 hours with stirring, then cooled to room temperature, filtered, the residue is washed with dry acetonitrile, and the filtrate is distilled. This gives 2.28 parts of the compound of the formula

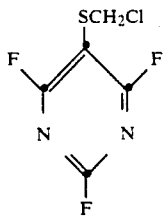

(102)

Example 3

60 parts of acetic acid (98–100 %) and 18.9 parts of acetic anhydride are initially introduced. 17.42 part of dried barbituric acid are then stirred into this solution, and 40.76 parts of dibenzyl sulfoxide are quickly poured into the resulting suspension.

The suspension is heated to $90°$ over a period of 2 hours and maintained at $90°$ to $100°$ for 4 hours. The precipitate obtained is filtered off at room temperature, washed with 50 parts of water, then with 40 parts of acetone, and then dried in vacuo at $40°$. This gives 38.5 parts of an intermediate. 90 parts of phosphorus oxychloride are initially introduced, and 6.94 parts of N,N-dimethylanaline are added dropwise. 38.5 parts of the intermediate obtained by the above procedure are stirred into this solution. The suspension is then heated and refluxed for 17 hours. After cooling to room temperature, excess phosphorus oxychloride is distilled off, the viscose residue is poured into 60 parts of water, and the temperature of the suspension kept at 25 to $30°$.

The suspension is then extracted with chloroform, the chloroform is separated off, and the reaction product is distilled in a high vacuum. This gives 24.58 parts of the compound of the formula

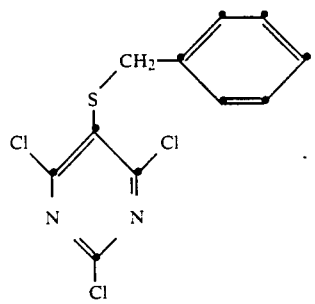

(103)

Example 4

The procedure of Example 2 is repeated, except that an equimolar amount of the compound of the formula (103) is used instead of 5.02 parts of the compound of the formula (101), to give the compound of the formula

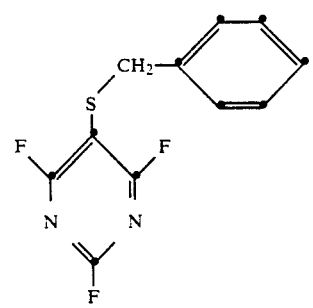

(104)

Example 5

6.62 parts of the chromophore of the formula

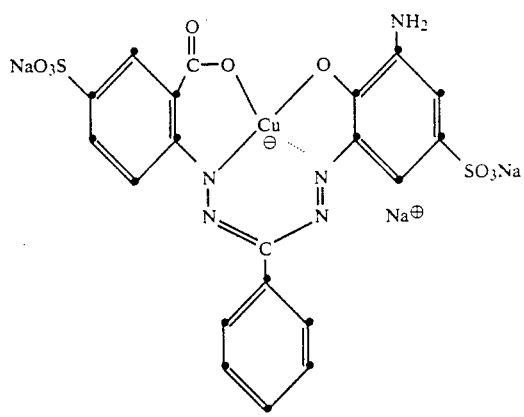

are stirred into 50 parts of water. The pH is adjusted to 7 by addition of hydrochloric acid.

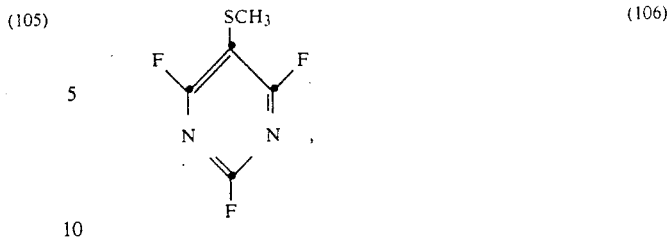

dissolved in 15 parts of acetone, are then added at 0° to 5° over a period of 3 minutes. The pH is maintained at 6 to 7 by addition of sodium hydroxide solution. The temperature is slowly raised to room temperature, while maintaining the pH at 6 to 7.

Sodium chloride is then added to the reaction solution, the precipitated dye is filtered off and dried at 60° to 70°. This gives 9.5 parts of a dye which conforms to the formula

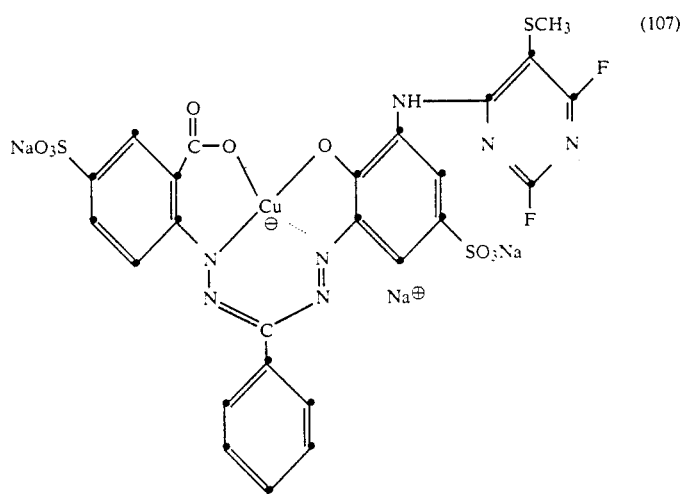

2.1 parts of the compound of the formula

The dye obtained dyes wool in blue shades which have good fastness properties.

Examples 6 to 24

The procedure as described in Example 5 is repeated, and the chromophores listed in column 2 of Table 1 are reacted with the pyrimidine compounds listed in column 3, to give analogous dyes which dye wool or cotton in the hue listed in column 4.

TABLE 1

| Ex. | Chromophore | Pyrimidine compound | Hue on cotton or wool |
|---|---|---|---|
| 6 | ![chromophore structure with SO3Na, NaO3S, SO3Na, NH-C(=O)-NH2, N=N, NH2 groups] (108) | ![pyrimidine with SCH3, F, F, N, N, F] | yellow |

TABLE 1-continued

| Ex. | Chromophore | Pyrimidine compound | Hue on cotton or wool |
|---|---|---|---|
| 7 | (108) | SCH₂Cl, F, F, N, N, F | yellow |
| 8 | (109) | SCH₃, F, F, N, N, F | yellow |
| 9 | (109) | SCH₂Cl, F, F, N, N, F | yellow |
| 10 | (110) | SCH₃, F, F, N, N, F | bluish red |
| 11 | (110) | SCH₂Cl, F, F, N, N, F | bluish red |
| 12 | (111) | SCH₃, F, F, N, N, F | red |

TABLE 1-continued

| Ex. | Chromophore | Pyrimidine compound | Hue on cotton or wool |
|---|---|---|---|
| 13 | (112) | SCH₂Cl, F, F, N, N, F | red |
| 14 | (113) | SCH₃, F, F, N, N, F | blue |
| 15 | (114) | SCH₃, F, F, N, N, F | yellow |
| 16 | (114) | SCH₂Cl, F, F, N, N, F | yellow |
| 17 | (115) | SCH₃, F, F, N, N, F | blue |

TABLE 1-continued
| Ex. | Chromophore | Pyrimidine compound | Hue on cotton or wool |
|---|---|---|---|
| 18 | 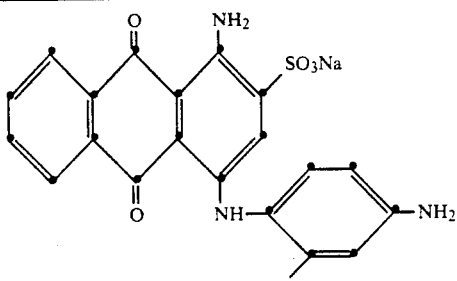 (115) | 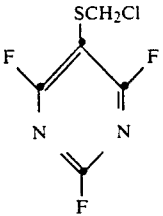 | blue |
| 19 | 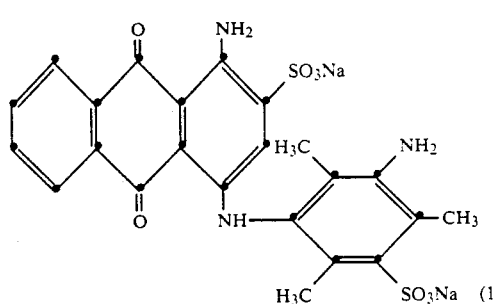 (116) | 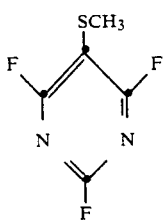 | blue |
| 20 | 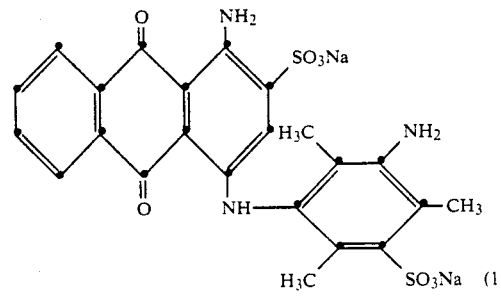 (116) | 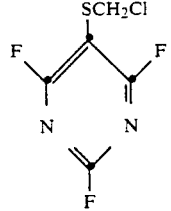 | blue |
| 21 | 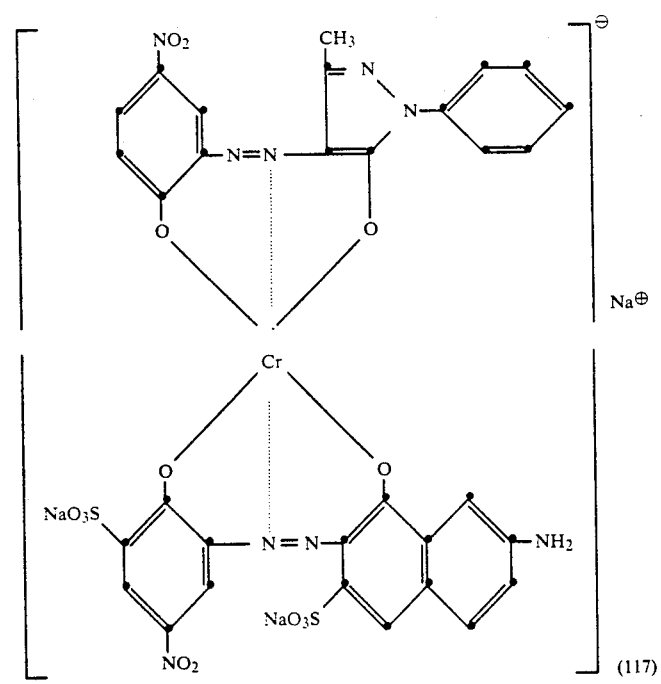 (117) | 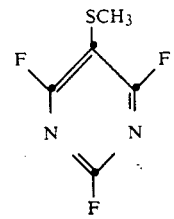 | brown |

TABLE 1-continued
| Ex. | Chromophore | Pyrimidine compound | Hue on cotton or wool |
|---|---|---|---|
| 22 | 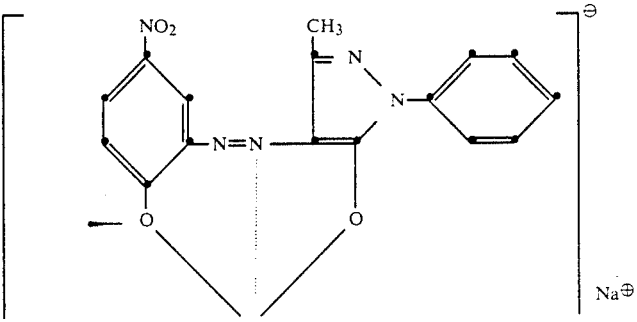 | 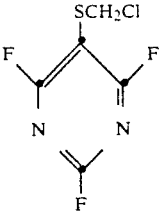 | brown |
| 23 | 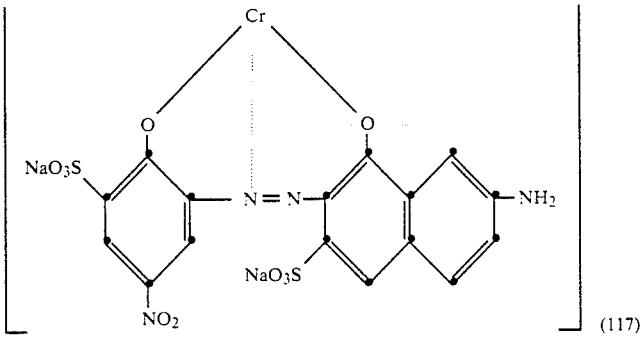 | 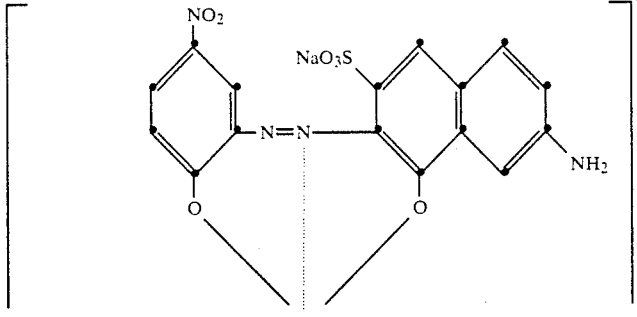 | black |

TABLE 1-continued

| Ex. | Chromophore | Pyrimidine compound | Hue on cotton or wool |
|---|---|---|---|
| 24 | (118) | SCH₂Cl, F, F, F (pyrimidine) | black |

Example 25

6.62 parts of the chromophore of the formula (105) from Example 5 are introduced into 50 parts of water. The pH is adjusted to 7 by addition of hydrochloric acid. 2.4 parts of the compound of the formula

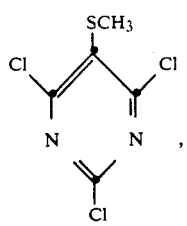
(119)

dissolved in 40 parts of acetone, are then added. The pH is maintained at 7 to 7.5 by addition of sodium hydroxide solution.

The mixture is then stirred at 40° and a pH of 7 to 7.5 for 8 hours, the reaction solution is filtered, sodium chloride is added to the filtrate, the precipitated dye is filtered off, washed with sodium chloride solution and dried at 60° to 70°.

This gives 10.8 parts of a dye which conforms to the formula

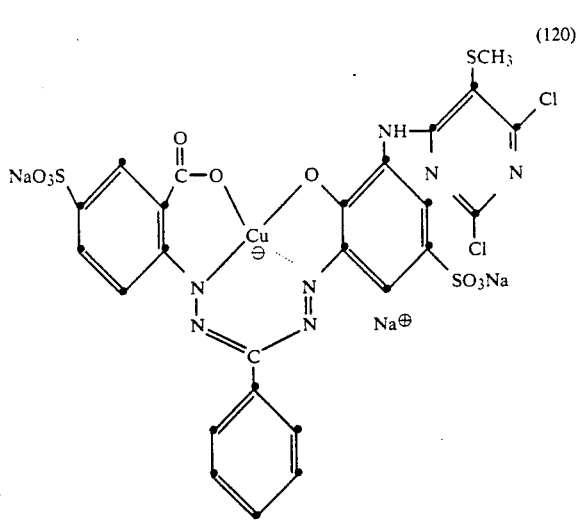
(120)

The dye obtained dyes wool in blue shades which have good fastness properties.

Examples 26 to 29

The procedure as described in Example 25 is repeated and the chromophores listed in column 2 of Table 2 are reacted with the pyrimidine compounds listed in column 3, to give analogous dyes which dye wool or cotton in the hue listed in column 4.

TABLE 2

| Ex. | Chromophore | Pyrimidine compound | Hue on cotton or wool |
|---|---|---|---|
| 26 | 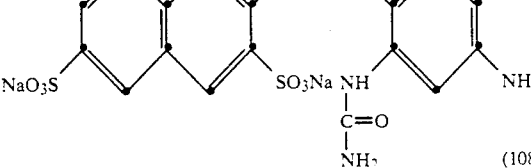 (108) | 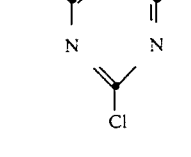 | yellow |
| 27 | 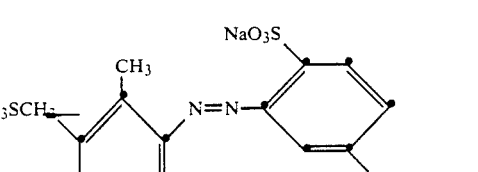 (109) | 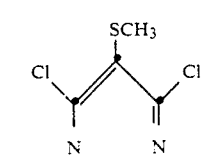 | yellow |
| 28 | 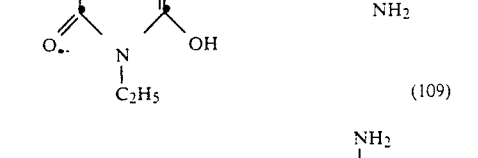 (113) | 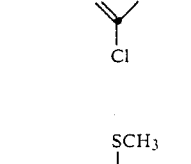 | blue |
| 29 | 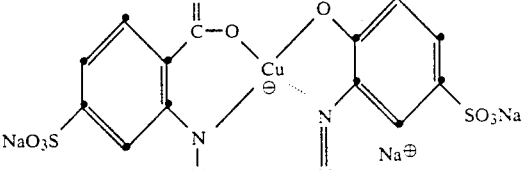 (105) | 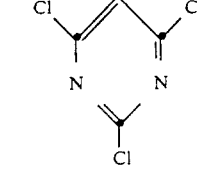 | blue |

Dying Example 1

4 parts of 80 % acetic acid, 2 parts of the ammonium salt of the monosulfate of the adduct of a fatty amine (consisting of 30 % of hexadecylamine, 25 % of octadecylamine and 45 % of octadecenylamine and 7 mol of ethylene oxide) and 4 parts of ammonium sulfate are dissolved in 4000 parts of water at 50°.

4 parts of the dye obtained according to Example 5 are dissolved in 100 parts of hot water and added to the above dye bath, which is then entered with 100 parts of pre-wetted wool knitwear, and the temperature of the bath is increased from 50 to 80° over a period of 30 minutes. After dyeing for 20 minutes at 80°, the bath is heated to boiling, and dyeing is then carried out at the boiling temperature for 90 minutes. The dye is almost completely absorbed by the substrate. After the bath has been cooled to 80°, the pH is increased from about 4.5 to a constant value of 8.5 by addition of ammonia solution, and the dyed material is after-treated at this temperature for 20 minutes. Thorough rinsing with hot and cold water, acidification with 1 part of 80 % formic acid, centrifugation and drying gives a blue-coloured wool yarn which has very good wet and rub fastness and excellent light fastness.

Dyeing Example 2

A wool fabric which has been given a non-felting finish is soaked in the preparation described below and squeezed off on a padder to a moisture pickup of 250 %:

| | |
|---|---|
| 4 | parts of Diaprint REG (acid-resistant thickener), |
| 1 | part of sulfamic acid |
| 0.2 | part of thymol |
| 0.2 | part of emulsifier |
| 94.6 | parts of water |
| 100 | parts |

The impregnated material is then pressed together in a heatable press for minutes at 100° to 105° under a pressure of about 0.5 kg/cm² with a transfer paper which carries a printing pattern applied in a customary manner by means of the dye according to Example 5. After rinsing and drying, the wool fabric exhibits the corresponding blue printing pattern which has very good fastness properties.

Dyeing Example 3

A flannel fabric made of chlorinated wool is soaked on a padder in a dye preparation described below and squeezed off to a liquid pickup of 100 %:

| | |
|---|---|
| 50 | parts of the dye according to Example 5 |
| 300 | parts of urea |
| 320 | parts of 40% Solvitose OFA (thickener) |
| 10 | parts of a mixture of anion-active fatty alcohol ether sulfate with nonionic wetting agents |
| 10 | parts of the levelling agent used in Dyeing Example 1 |
| 10 | parts of sodium metabisulfite |
| 10 | parts of 80% acetic acid |
| 290 | parts of water |
| 1000 | parts of padding liquor |

The impregnated fabric is then left at room temperature for 48 hours in a rolled-up and airtight sealed state. After rinsing with cold water, the material is treated in a fresh bath with 24 % ammonia solution, until a pH of 8.5 has been reached, and maintained at 80° for 15 minutes. After rinsing in warm water, it is finally acidified with 80 % acetic acid and dried. The wool fabric has been dyed in a full blue shade which has excellent fastness properties.

Dyeing Example 4

A flannel fabric made of chlorinated wool is soaked on a padder in a dye preparation described below and squeezed off to a liquid pickup of 100 %:

| | |
|---|---|
| 50 | parts of the dye according to Example 5 |
| 300 | parts of 40% Solvitose OFA (thickener) |
| 20 | parts of a mixture of anion-active fatty alcohol ether sulfate with nonionic wetting agents |
| 10 | parts of the levelling agent used in Dyeing Example 1 |
| 20 | parts of 80% acetic acid |
| 600 | parts of water |
| 1000 | parts of padding liquor |

The impregnated fabric is then transferred to a steamer and treated with saturated steam for 20 to 40 minutes. After rinsing with cold water, the material is treated in a fresh bath with 24 % ammonia solution, until a pH of 8.5 has been reached, and maintained at 80° for 15 minutes. After rinsing in warm water, it is finally acidified with 80 % acetic acid and dried. The wool fabric has been dyed in a full blue shade which has excellent fastness properties.

Dyeing Example 5

4 parts of 80 % acetic acid, 2 parts of the ammonium salt of the monosulfate of the adduct of a fatty amine (consisting of 30 % of hexadecylamine, 25 % of octadecylamine and 45 % of octadecenylamine and 7 mol of ethylene oxide) and 4 parts of ammonium sulfate are dissolved in succession in 1000 parts of water at 50°.

3 parts of the dye obtained according to Example 5 are dissolved in 100 parts of hot water and added to the above dye bath. A circulation dyeing machine is charged with 100 parts of pre-wetted tubs in wound form, and the temperature of the bath is raised from 50° to 97°-99° over a period of 30 minutes, and dyeing is then carried out at the boiling temperature for 90 minutes. The dye is almost completely absorbed by the substrate. After the bath has been cooled to 80°, the pH is increased from about 4.5 to a constant value of 8.5 by addition of ammonia solution, and the dyed material is after-treated at this temperature. Thorough rinsing with hot and cold water, acidification with 1 part of 80 % formic acid, centrifugation and drying gives a blue-coloured dyed material which has very good wet fastness and excellent light fastness.

Dyeing Example 6

6 parts of 80 % acetic acid, 3 parts of the ammonium salt of the monosulfate of the adduct of a fatty amine (consisting of 30 % of hexadecylamine, 25 % of octadecylamine and 45 % of octadecenylamine and 7 mol of ethylene oxide) and 6 parts of ammonium sulfate are dissolved in succession in 1000 parts of water at 50°.

3 parts of the dye obtained according to Example 5 are dissolved in 100 parts of hot water and added to the above dye bath. A circulation dyeing machine ia charged with 150 parts of pre-wetted loose wool, and the temperature of the bath is raised from 50° to 97°-99° over a period of 30 minutes, and dyeing is then carried out at the boiling temperature for 90 minutes. The dye is almost completely absorbed by the substrate. After the bath has been cooled to 80°, the pH is increased from about 4.5 to a constant value of 8.5 by addition of ammonia solution, and the dyed material is after-treated at this temperature. Thorough rinsing with hot and cold water, acidification with 1 part of 80 % formic acid, centrifugation and drying gives a level blue dyeing on the substrate which has good wet and rub fastness and excellent light fastness.

Dyeing Example 7

2 parts of the dye obtained according to Example 6 are dissolved in 400 parts of water; 1500 parts of a solution containing 53 g of sodium chloride per litre are than added. This dye bath is entered at 40° with 100 parts of a cotton fabric. After 45 minutes, 100 parts of a solution containing 16 g of sodium hydroxide and 20 g of calcined sodium carbonate per litre are added. The temperature of the dye bath is maintained at 40° for another 45 minutes. The dyed material is then rinsed, soaped at the boiling temperature by means of a nonionic detergent for quarter of an hour, rinsed again and dried.

What is claimed is:

1. A reactive dry of the formula

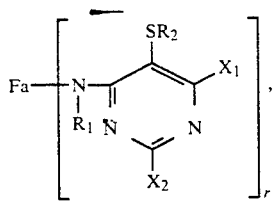

(1)

in which Fa is the radical of an organic dye of the monoazo or polyazo, metal complex azo, anthraquinone, phthalocyanine, formazan, azomethine, dioxazine, phenazine, stilbene, triphenylmethane, xanthene, thioxanthone, nitroaryl, naphthoquinone, pyrenequinone or perylene-tetracarbimide series, $X_1$ and $X_2$, independently of one another, are each halogen, $R_1$ is hydrogen or $C_1-C_4$alkyl which is unsubstituted or substituted by halogen, hydroxy, cyano, carboxy, sulfo, sulfato, $C_1-C_4$alkoxycarbonyl or $C_1-C_4$alkoxy, $R_2$ is $C_1-C_4$alkyl which is unsubstituted or substituted by halogen or phenyl and r is the number 1 or 2.

2. A reactive dye according to claim 18, wherein r is the number 1.

3. A reactive dye according to claim 18, wherein $X_1$ and $X_2$, independently of one another, are each chlorine or fluorine.

4. A reactive dye according to claim 18, wherein $X_1$ and $X_2$ are each chlorine or fluorine.

5. A reactive dye according to claim 18, wherein $R_1$ is methyl, ethyl or hydrogen.

6. A reactive dye according to claim 18, wherein $R_2$ is unsubstituted or halogen-, or phenyl-substituted methyl or ethyl.

7. A reactive dye according to claim 18, wherein $R_2$ is methyl, monochloromethyl or benzyl.

8. A reactive dye according to claim 18, wherein Fa is unsubstituted or substituted by unsubstituted or sulfo-substituted $C_1-C_4$alkyl, $C_1-C_4$-alkoxy, phenyl, $C_1-C_4$alkanoylamino, benzoylamino, amino, N-mono- or N,N-di-$C_1-C_4$alkylamino which is unsubstituted or substituted in the alkyl moiety by —OH, —OCOCH$_3$, —OSO$_3$H, —CN or halogen, unsubstituted or sulfo- and/or $C_1-C_4$alkyl-substituted phenylamino, mono- or di-sulfobenzylamino, $C_1-C_4$alkoxycarbonyl, $C_1-C_4$alkylsulfonyl, trifluoromethyl, nitro, cyano, halogen, carbamoyl, N-mono-or N,N-di-$C_1-C_4$alkylcarbamoyl, sulfamoyl, N-mono- or N,N-di-$C_1-C_4$alkylsulfamoyl, N-mono- or N,N-di-($\beta$-hydroxyethyl)sulfamoyl, N-phenylsulfamoyl, hydroxy, carboxy, sulfo, sulfomethyl and/or ureido.

9. A reactive dye according to claim 18 wherein Fa is the radical of an organic dye of the monoazo or polyazo., metal complex azo, anthraquinone, phthalocyanine, formazan or dioxazine series, which is substituted by one or more of the radicals mentioned in claim 8.

10. A reactive dye of the formula (1) according to claim 18 in which Fa is the radical of an organic dye of the monoazo or polyazo, metal complex azo, anthraquinone, phthalocyanine, formazan or dioxazine series, which carries one or more sulfo groups and may be further substituted by one or more of the radicals mentioned in claim 8, $R_1$ is hydrogen or unsubstituted or halogen- hydroxyl-, cyano-, carboxyl-, sulfo-, sulfato-, $C_1-C_4$alkoxycarbonyl or $C_1-C_4$alkoxy-substituted $C_1-C_4$alkyl, $X_1$ and $X_2$, independently of one another, are each chlorine or fluorine, $R_2$ is unsubstituted or halogen-, or phenyl-substituted methyl or ethyl and r is the number 1.

11. A reactive dye according to claim 10 of the formula

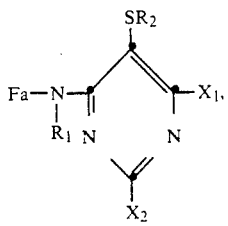

(2)

in which Fa is as defined in claim 10, $R_1$ is hydrogen, methyl or ethyl, $X_1$ and $X_2$ are each chlorine or fluorine and $R_2$ is methyl, monochloromethyl or benzyl.

12. A reactive dye according to claim 18 of the formula

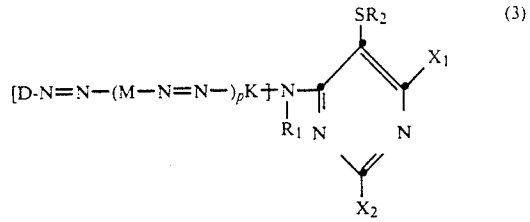

(3)

or

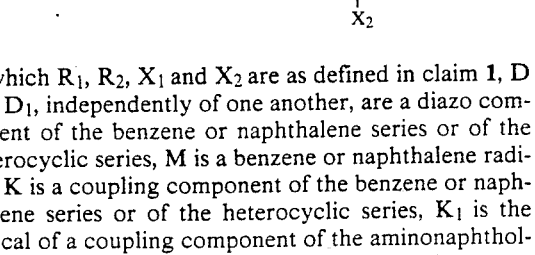

(4)

in which $R_1$, $R_2$, $X_1$ and $X_2$ are as defined in claim 1, D and $D_1$, independently of one another, are a diazo component of the benzene or naphthalene series or of the heterocyclic series, M is a benzene or naphthalene radical; K is a coupling component of the benzene or naphthalene series or of the heterocyclic series, $K_1$ is the radical of a coupling component of the aminonaphtholsulfonic acid series and p is the number 0 or 1.

13. A reactive dye according to claim 18 of the formulae

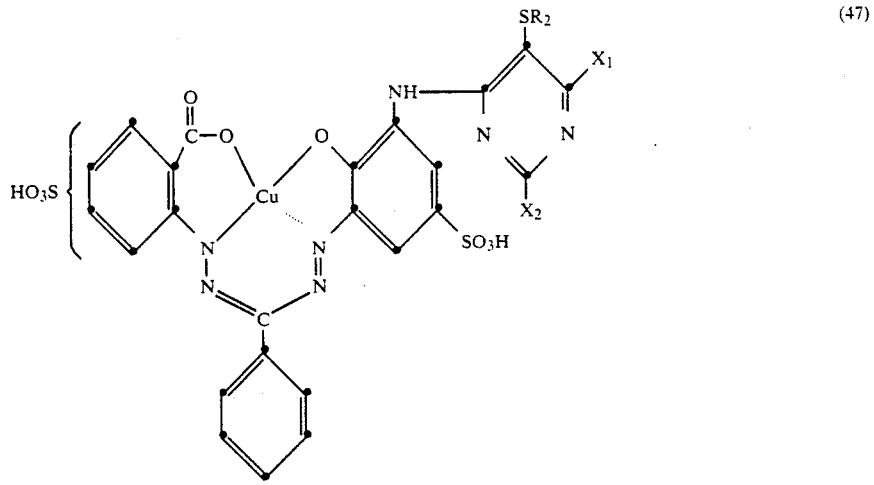
(47)
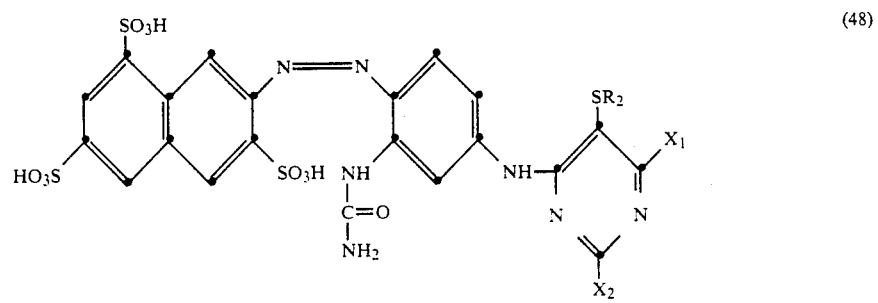
(48)
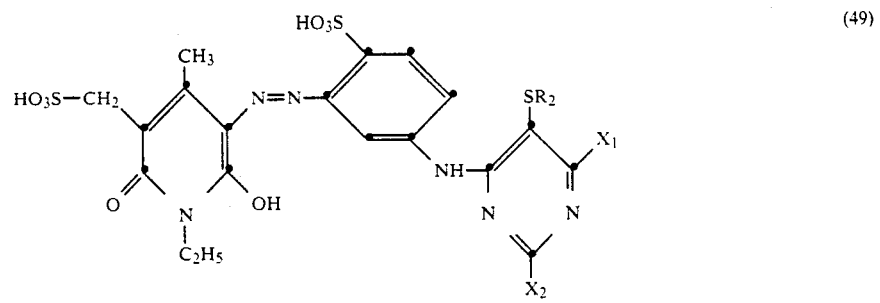
(49)
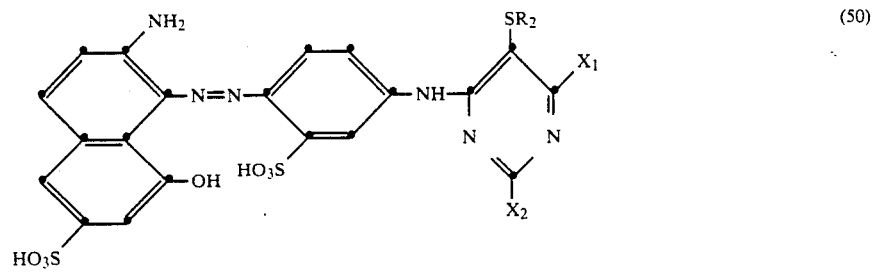
(50)
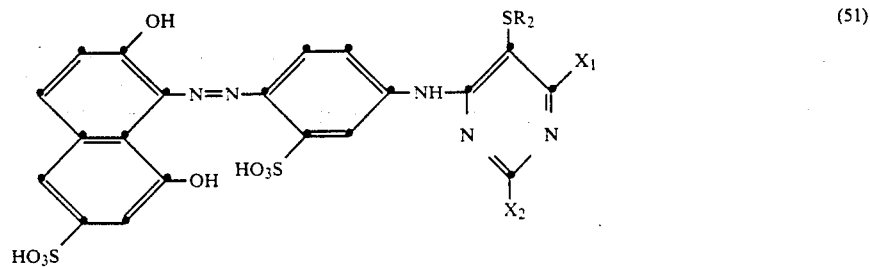
(51)

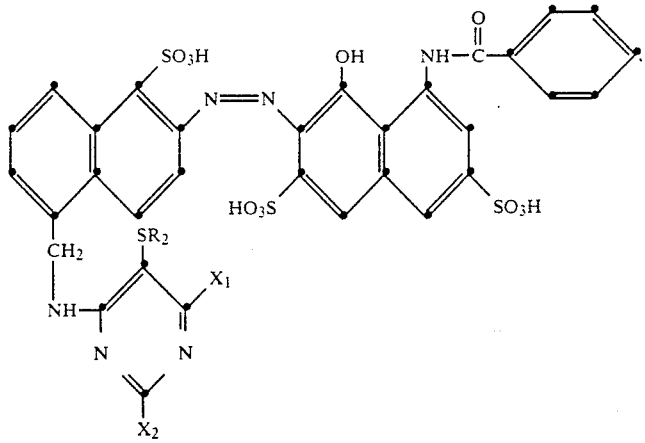
(52)
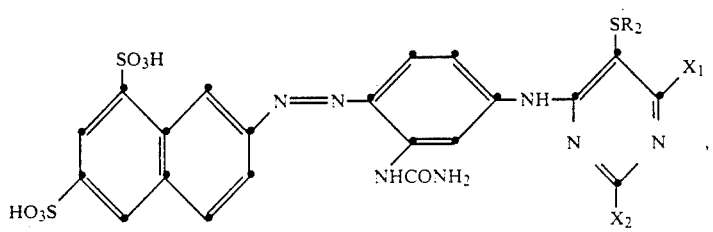
(53)
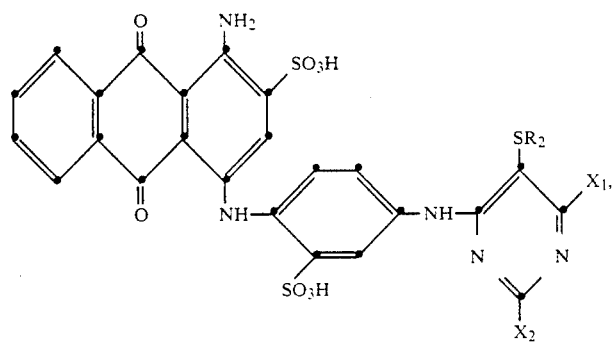
(54)
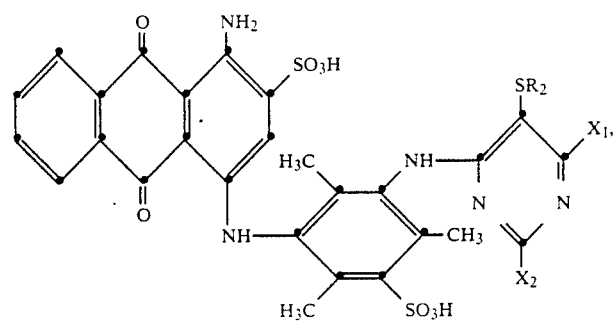
(55)
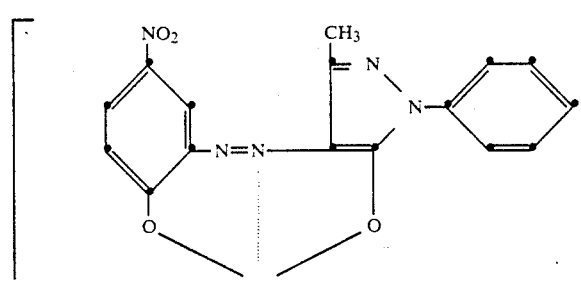
(56)

-continued

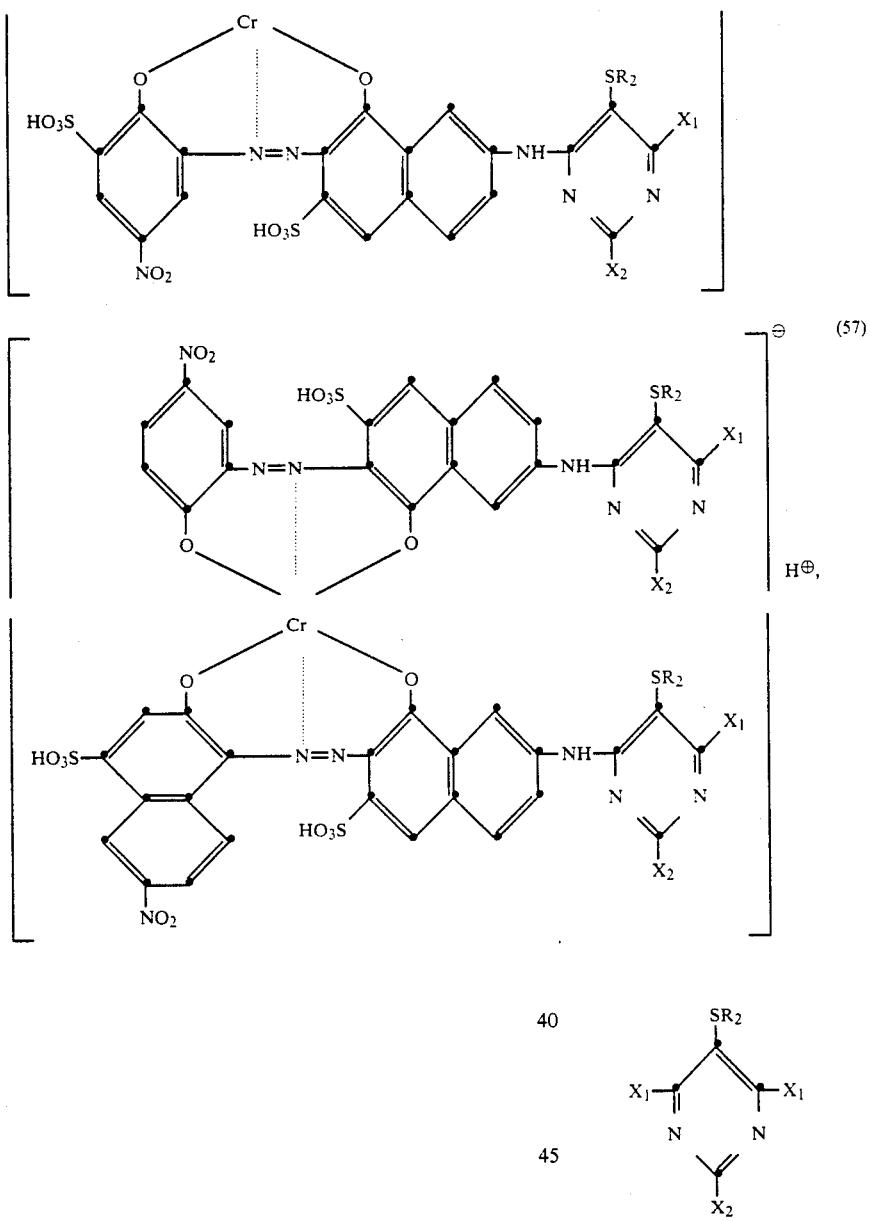

in which $R_2$, $X_1$ and $X_2$ are as defined in claim 1.

14. A process for the preparation of reactive dyes according to claim 18 which comprises condensing an organic dye of the formula $$Fa\left[\begin{matrix}N-H\\|\\R_1\end{matrix}\right]_r \quad (58)$$

or a dye precursor with at least one equivalent of a pyrimidine derivative of the formula to give a reactive dye of the formula (1) in which Fa, $R_1$, $R_2$, $X_1$, $X_2$ are r are as defined in claim 1.

15. A reactive dye according to claim 5, wherein $R_1$ is hydrogen.

16. A reactive dye according to claim 6, wherein $R_2$ is unsubstituted or chlorine- or phenyl-substituted methyl or ethyl.

17. A reactive dye according to claim 10, wherein $R_2$ is unsubstituted or chlorine- or phenyl-substituted methyl or ethyl.

18. A method for dyeing and printing hydroxyl and nitrogen containing textile materials comprising the application of a tinctoral amount of at least one dye according to claim 18 to the textile material.

19. A method of claim 18 wherein the textile material is cotton or wool.

* * * * *

UNITED STATES PATENT AND TRADEMARK OFFICE
CERTIFICATE OF CORRECTION

PATENT NO. : 5,037,449
DATED : August 6, 1991
INVENTOR(S) : Karl Hoegerle and Urs Lehmann It is certified that error appears in the above-identified patent and that said Letters Patent is hereby corrected as shown below:

Col. 47, Claim 1, line 16, should read:

--1. A reactive dye of the formula--.

Signed and Sealed this

Twenty-second Day of December, 1992

Attest:

DOUGLAS B. COMER

*Attesting Officer*    *Acting Commissioner of Patents and Trademarks*